US007622635B2

(12) United States Patent
Hemerly et al.

(10) Patent No.: US 7,622,635 B2
(45) Date of Patent: Nov. 24, 2009

(54) METHOD OF INCREASING YIELD IN PLANTS

(75) Inventors: Adriana Silva Hemerly, Rio de Janeiro (BR); Paulo Cavalcanti Gomes Ferreira, Rio de Janeiro (BR); Stephane Rombauts, Gent (BE)

(73) Assignees: CropDesign N.V., Gent (BE); Universidade Federal do Rio de Janeiro, Rio de Janeiro RJ (BR)

( * ) Notice: Subject to any disclaimer, the term of this patent is extended or adjusted under 35 U.S.C. 154(b) by 197 days.

(21) Appl. No.: 11/239,325

(22) Filed: Sep. 30, 2005

(65) Prior Publication Data

US 2006/0026720 A1 Feb. 2, 2006

Related U.S. Application Data

(60) Division of application No. 10/036,492, filed on Jan. 7, 2002, now abandoned, which is a continuation of application No. PCT/EP00/06401, filed on Jul. 5, 2000.

(30) Foreign Application Priority Data

Jul. 5, 1999 (EP) .................................. 99202214

(51) Int. Cl.
*C12N 15/82* (2006.01)
*A01H 5/00* (2006.01)

(52) U.S. Cl. ....................... 800/290; 800/287; 435/419; 435/468

(58) Field of Classification Search ....................... None
See application file for complete search history.

(56) References Cited

FOREIGN PATENT DOCUMENTS

| | | |
|---|---|---|
| WO | WO 96/31608 | 10/1996 |
| WO | WO 98/41642 | 9/1998 |
| WO | WO 01/02430 A2 | 1/2001 |
| WO | WO 01/02430 A3 | 1/2001 |

OTHER PUBLICATIONS

Kumar P. et al. Depletion of anaphase-promoting complex or cyclosome (APC/C) subunit homolog APC1 or CDC27 of *Trypanosoma brucei* arrests the procyclic form in metaphase but the bloodstream form in anaphase. J Biol Chem. Sep. 9, 2005;280(36):31783-91. Epub Jul. 1, 2005.*

Paquet M.E. et al. Analysis of several endoglin mutants reveals no endogenous mature or secreted protein capable of interfering with normal endoglin function. Hum Mol Genet. Jun. 15, 2001;10(13):1347-57.*

Rounsley, et al., EMBL Accession No. B78168 T31I20TF TAMU *Arabidopsis Tthaliana* Genomic Clone T31I20TF, Genomic Surve Seuence, Jan. 16, 1998.

Zhou, et al., The Plant Cyclin-Dependent Kinase Inhibitor ICK1 has Distince Dunctional domains for a Vivo Kinase Inhibition, Protein Instability and Nuclear Localization. Plan J., Aug. 2003, 25(4):476-89.

Hemerly, et al., Dominant Negative Mutants of the Cdc2 Kinase Uncouple Cell Division from Interative Plant Development. EMBO J., Aug. 15, 1995, 14(16):3925-36.

Kinase Point Mutants; Dominant-Negative Inhibition of DNA Replication on Overexpression of Kinase-Negative Cdc7 Proteins, Molecular and General Genetics, vol. 254., No. 5, May 20, 1997, pp. 562-570, I.D. XP002157233.

Hamer, et al., M.J., et al., "Control of Initiation of DNA Synthesis in Plants," Proceedings of the Phytochemical society of Europe, vol. 39, 1996, pp. 211,224, I.D., XP-000926262.

Hemerly, A., et al., "Dominant Negative Mutants of the Cc2 Kinase Uncouple Cell Division from Interative Plant Development," EMBO Journal, vol. 14, No. 16, Aug. 15, 1995, I.D. XP-002045514.

Bevan, M., et al., "Analysis of 1.9 Mb of Contiguous Sequence from Chromosome 4 of *Arabidopsis thaliana*,"Nature, vol. 391, No. 6666, Jan. 29, 1998, pp. 485-488, XP002157232 Abstract.

Bevan, M., et al., Sequence Listing Segments, I.D., XP-002157235 and XP-002157234. Accession 023540 Jan. 1, 1998; Accession Z97342 Jul. 4, 1997.

Masai, J., et al., "HSKL, a *Schizosaccharomyces pombe* gene Related to *Saccharomces cerevisiae* CDC7, is Required for Chromosomal Replication,": EMBO Journal, vol. 15, No. 13, Jul. 3, 1995, pp. 3094-3104, I.D., XP-00978701.

Mizoguchi, T., et al., "ATMPKs: A Gene Family of Plant MAP Kinases in *Arabidopsis thailiana*," FEBS Letters, vol. 336, No. 3, Dec. 28, 1993, pp. 440-444, I.D. XP-002079537.

Ohtoshi, A., et al., Analyses of *Saccharomyces cerevisiae* Cdc7 Kinase Point Mutants: Dominant-Negative Inhibition of DNA Replication on Overexpression of Kinase-Negative Cdc7 Proteins, Molecular and General Genetics., vol. 254, No. 5, May 20, 1997, pp. 562-570, ID XP-002157233.

Hammer, M.J., et al., Control of Initiation of DNA Synthesis in Plants, Proceedings of the Phytochemical Society of Europe, vol. 39, 1996, pp. 211, 224, ID XP-000926262.

Hemerly, et al., "Dominant Negative Mutants of the Cc2 Kinase Uncouple Cell Division from Iterative Plant Development," EMBO Journal., vol. 14, No. 16, Aug. 15, 1995, pp. 3925-3936, I.D. XP-002045514.

Lamb, J.R., et al., Tetratrico Peptide Repeat Interactions: to TPR or not to TPR? Trends Biochem. Sc., Jul. 1995, 20(7):257-9.

* cited by examiner

*Primary Examiner*—Cynthia Collins
(74) *Attorney, Agent, or Firm*—Oblon, Spivak, McClelland, Maier & Neustadt, L.L.P.

(57) ABSTRACT

The present invention provides a method of increasing yield in plants, comprising transforming a plant with a nucleic acid encoding a CDC27 polypeptide or homolog thereof having a N-terminal deletion operably linked to a promoter active in the plant, where 100 to 220 amino acids are deleted at the N-terminus of the CDC27 polypeptide.

10 Claims, 16 Drawing Sheets

Fig. 3

```
                          |1
                          ATGTCAGAAAACTCGGAACCGCGTCAACTCGAGAATTCTACA
  1 ---------+---------+---------+---------+---------+---------+ 60
    TCTAAGTGTCGTAAACGTTACAGTCTTTTGAGCCTTGGCGCAGTTGAGCTCTTAAGATGT

                          |1
                          M  S  E  N  S  E  P  R  Q  L  E  N  S  T  -

    GCCGGAAGAGAGCTCATTCCTCTTAGTCCCACCAATTCAGACGGCAACGACGACCTTAAC
 61 ---------+---------+---------+---------+---------+---------+ 120
    CGGCCTTCTCTCGAGTAAGGAGAATCAGGGTGGTTAAGTCTGCCGTTGCTGCTGGAATTG

    A  G  R  E  L  I  P  L  S  P  T  N  S  D  G  N  D  D  L  N  -

    TATCATCTGCATGCTTTTGAGTTATCTCGTCTCCTACTTTCTTCTGGTCATCCAGAATCT
121 ---------+---------+---------+---------+---------+---------+ 180
    ATAGTAGACGTACGAAAACTCAATAGAGCAGAGGATGAAAGAAGACCAGTAGGTCTTAGA

    Y  H  L  H  A  F  E  L  S  R  L  L  L  S  S  G  H  P  E  S  -

    GTTATAGATCTTTCTTCAAAGTGTACATACTTCCAAGGTTCTCCTAATCTCGTCAAATAT
181 ---------+---------+---------+---------+---------+---------+ 240
    CAATATCTAGAAAGAAGTTTCACATGTATGAAGGTTCCAAGAGGATTAGAGCAGTTTATA

    V  I  D  L  S  S  K  C  T  Y  F  Q  G  S  P  N  L  V  K  Y  -

    CTTTGCTCGATCCCTAATTCTCCTATTTCCCTTGCCGAAGATGGCTTCACTGTGACTCTC
241 ---------+---------+---------+---------+---------+---------+ 300
    GAAACGAGCTAGGGATTAAGAGGATAAAGGGAACGGCTTCTACCGAAGTGACACTGAGAG

    L  C  S  I  P  N  S  P  I  S  L  A  E  D  G  F  T  V  T  L  -

    TCGCCTGAGTCTCCCTCCGCTCCGGCTAGTTTCGCCTGTAGTTTGGATTTGCAGGAAAAT
301 ---------+---------+---------+---------+---------+---------+ 360
    AGCGGACTCAGAGGGAGGCGAGGCCGATCAAAGCGGACATCAAACCTAAACGTCCTTTTA

    S  P  E  S  P  S  A  P  A  S  F  A  C  S  L  D  L  Q  E  N  -

                                                         1|2
    GTTGTGTTAGAACAGTTTATGGATCCGAGATCTCTCACGCTAAAGCATTCGAGAGAGAAT
361 ---------+---------+---------+---------+---------+---------+ 420
    CAACACAATCTTGTCAAATACCTAGGCTCTAGAGAGTGCGATTTCGTAAGCTCTCTCTTA
                                                         1|2
    V  V  L  E  Q  F  M  D  P  R  S  L  T  L  K  H  S  R  E |N  -

    GCGGAACAAGAGGAGCTAGAGCTCATGCCATTGCCCAAAAGAAGTCGAAATGATGGAAAC
421 ---------+---------+---------+---------+---------+---------+ 480
    CGCCTTGTTCTCCTCGATCTCGAGTACGGTAACGGGTTTTCTTCAGCTTTACTACCTTTG

    A  E  Q  E  E  L  E  L  M  P  L  P  K  R  S  R  N  D  G  N  -
```

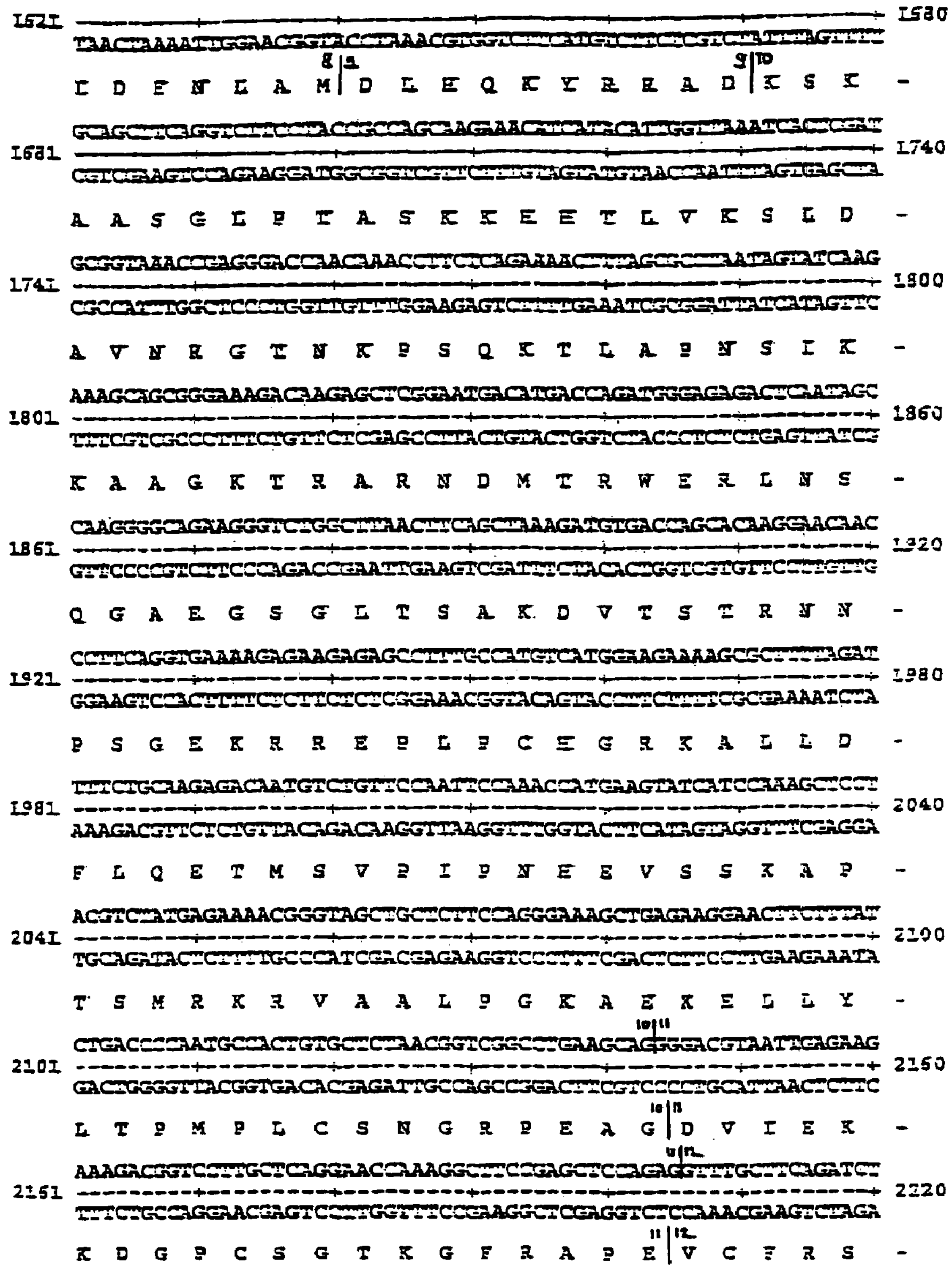

Fig. 3 continued

```
1621 ----------+---------+---------+---------+---------+---------+ 1680
     TAACTAAAATGGAACGGTACCTAAACGNGGTCNNATGTCTCCGTCTATTAGTTTC
                    g|a                              9|10
      L  D  F  N  L  A  M |D  L  E  Q  K  Y  R  R  A  D |K  S  L  -

     GCAGCTTCGGTCTTCCTACCGCCAGCAGAACGTCATCATGGTNAAATCGCCGAT
1681 ----------+---------+---------+---------+---------+---------+ 1740
     CGTCGAAGTCCAGAAGGATGGCGGTCGTCTTGTAGTAGTACNATTTAGTGGCTA
      A  A  S  G  L  P  T  A  S  K  K  E  E  T  L  V  K  S  L  D  -

     GCGGTAAACCGAGGGACCAACAAACCTTCTCAGAAACGTTAGCGCNAATAGTATCAAG
1741 ----------+---------+---------+---------+---------+---------+ 1800
     CGCCATTTGGCTCCCTGGTTGTTTGGAAGAGTCTTTGAAATCGCGNTTATCATAGTTC
      A  V  N  R  G  T  N  K  P  S  Q  K  T  L  A  N  S  I  K  -

     AAAGCAGCGGGAAAGACAAGAGCTCGGAATGACATGACCAGATGGAGAGACTCAATAGC
1801 ----------+---------+---------+---------+---------+---------+ 1860
     TTTCGTCGCCCTTTCTGTTCTCGAGCCTTACTGTACTGGTCTACCTCCTGAGTTATCG
      K  A  A  G  K  T  R  A  R  N  D  M  T  R  W  E  R  L  N  S  -

     CAAGGGCAGAAGGGTCTGGCTTAACTTCAGCTAAAGATGTGACCAGCACAAGGAACAAC
1861 ----------+---------+---------+---------+---------+---------+ 1920
     GTTCCCCGTCTTCCCAGACCGAATTGAAGTCGATTTCTACACTGGTCGTGTTCCTTGTTG
      Q  G  A  E  G  S  G  L  T  S  A  K  D  V  T  S  T  R  N  N  -

     CCTTCAGGTGAAAAGAGAAGAGAGCCTTTGCCATGTCATGGAAGAAAAGCGCTTTTAGAT
1921 ----------+---------+---------+---------+---------+---------+ 1980
     GGAAGTCCACTTTTCTCTTCTCTCGGAAACGGTACAGTACCTTCTTTTCGCGAAAATCTA
      P  S  G  E  K  R  R  E  P  L  P  C  H  G  R  K  A  L  L  D  -

     TTTCTGCAGAGACAATGTCTGTTCCAATTCCAAACCATGAAGTATCATCCAAAGCTCCT
1981 ----------+---------+---------+---------+---------+---------+ 2040
     AAAGACGTCTCTGTTACAGACAAGGTTAAGGTTTGGTACTTCATAGTAGGTTTCGAGGA
      F  L  Q  E  T  M  S  V  P  I  P  N  E  E  V  S  S  K  A  P  -

     ACGTCTATGAGAAAACGGGTAGCTGCTCTTCCAGGGAAAGCTGAGAAGGAACTTCTTTAT
2041 ----------+---------+---------+---------+---------+---------+ 2100
     TGCAGATACTCTTTTGCCCATCGACGAGAAGGTCCCTTTCGACTCTTCCTTGAAGAAATA
      T  S  M  R  K  R  V  A  A  L  P  G  K  A  E  K  E  L  L  Y  -

                                            10|11
     CTGACCCCAATGCCACTGTGCTCTAACGGTCGGCCTGAAGCAGGGACGTAATTGAGAAG
2101 ----------+---------+---------+---------+---------+---------+ 2150
     GACTGGGGTTACGGTGACACGAGATTGCCAGCCGGACTTCGTCCCTGCATTAACTCTTC
                                            10|11
      L  T  P  M  P  L  C  S  N  G  R  P  E  A  G |D  V  I  E  K  -
                                                  11|12
     AAAGACGGTCCTTGCTCAGGAACCAAGGCTTCCGAGCTCCAGAGTTTGCTTCAGATCT
2151 ----------+---------+---------+---------+---------+---------+ 2220
     TTTCTGCCAGGAACGAGTCCTTGGTTCCGAAGGCTCGAGGTCTCAAACGAAGTCTAGA
                                                  11|12
      K  D  G  P  C  S  G  T  K  G  F  R  A  P  E |V  C  F  R  S  -
```

Fig. 3 continued

```
     TTGCACCAAGGACCTAAGATAGACGTGTGGTCTGCGGGAGTTACTTTGTTATACCTCATA
2221 ------------------------------------------------------------ 2280
     AACGTGGTTCCTGGATTCTATCTGCACACCAGACGCCCTCAATGAAACAATATGGAGTAT

     L  H  Q  G  P  K  I  D  V  W  S  A  G  V  T  L  L  Y  L  I  -
                                         12|13
     ATGGGAAGGACACCTTTCACTGGTGACCCTGAACAGAACATAAAGGACATTGCACAACTA
2281 ------------------------------------------------------------ 2340
     TACCCTTCCTGTGGAAAGTGACCACTGGGACTTGTCTTGTATTTCCTGTAACGTGTTGAT
                                         12|13
     M  G  R  T  P  F  T  G  D  P  E  Q |N  I  K  D  I  A  Q  L  -

     CGAGGCAGTGAAGAATTATGGGAAGTAGCCAAGCTGCACAACCGTGAATCCTCTTTCCCT
2341 ------------------------------------------------------------ 2400
     GCTCCGTCACTTCTTAATACCCTTCATCGGTTCGACGTGTTGGCACTTAGGAGAAAGGGA

     R  G  S  E  E  L  W  E  V  A  K  L  H  N  R  E  S  S  F  P  -
       13|14
     AAGGAATTATACGAGTCAAGGTACTTGAAGGGGATGGAGTTGAGAAAATGGTGCGAACTC
2401 ------------------------------------------------------------ 2460
     TTCCTTAATATGCTCAGTTCCATGAACTTCCCCTACCTCAACTCTTTTACCACGCTTGAG
     13|14
     K |E  L  Y  E  S  R  Y  L  K  G  M  E  L  R  K  W  C  E  L  -

     AACACAAAACGCAGAGAGTTTCTAGACGTAATTCCACTATCGCTTCTTGACCTCGTTGAT
2461 ------------------------------------------------------------ 2520
     TTGTGTTTTGCGTCTCTCAAAGATCTGCATTAAGGTGATAGCGAAGAACTGGAGCAACTA

     N  T  K  R  R  E  F  L  D  V  I  P  L  S  L  L  D  L  V  D  -

     AAATGTTTGACCGTTAACCCGAGGCGACGAATCAGCGCAGAGGATGCTCTCAAGCACGAC
2521 ------------------------------------------------------------ 2580
     TTTACAAACTGGCAATTGGGCTCCGCTGCTTAGTCGCGTCTCCTACGAGAGTTCGTGCTG

     K  C  L  T  V  N  P  R  R  R  I  S  A  E  D  A  L  K  H  D  -

     TTCTTCCATCCAGTACATGAAACCCTTAGAAACCAAATGCTCCTTAAACAGCAGCCTACA
2581 ------------------------------------------------------------ 2640
     AAGAAGGTAGGTCATGTACTTTGGGAATCTTTGGTTTACGAGGAATTTGTCGTCGGATGT

     F  F  H  P  V  H  E  T  L  R  N  Q  M  L  L  K  Q  Q  P  T  -
                                                     14|
     GTGGTTGCTGACGCAGTAAGCCAAACTCTAAACTATTTACAATTGTAAAAGTAAATAAG
2641 ----------------------------------------------------------- 2699
     CACCAACGACTGCGTCATTCGGTTTGAGATTTGATAAATGTTAACATTTTCATTTATTC

     V  V  A  D  A  V  S  Q  T  L  N  Y  L  Q  L  *
```

```
1   ---------+---------+---------+---------+---------+---------+ 60
    CCGCTGTAATGTGTGTGTCGGAGGCTCCTTGTTGTTGTTGTAGCTAACAGAGCAGTTAAA

     .  .  .  .  .  .  .  .  .  .  .  .  .  .  .  .  .  .  .  .

                      |1
                      |ATGATGGAGAATCTACTGGCGAATTGTGTCCAGAAAAACCTT
61  ---------+---------+---------+---------+---------+---------+ 120
    CCAGTAGTAGTAGTAGTCTACTACCTCTTAGATGACCGCTTAACACAGGTCTTTTTGGAA

                        |1
     .  .  .  .  .  .  |M  M  E  N  L  L  A  N  C  V  Q  K  N  L

    AACCATTTTATGTTCACCAATGCTATCTTCCTTTGCGAACTTCTTCTCGCCCAATTTCCA
121 ---------+---------+---------+---------+---------+---------+ 180
    TTGGTAAAATACAAGTGGTTACGATAGAAGGAAACGCTTGAAGAAGAGCGGGTTAAAGGT

     N  H  F  M  F  T  N  A  I  F  L  C  E  L  L  L  A  Q  F  P

         1|2
    TCTGAGGTGAACCTGCAATTGTTAGCCAGGTGTTACTTGAGTAACAGTCAAGCTTATAGT
181 ---------+---------+---------+---------+---------+---------+ 240
    AGACTCCACTTGGACGTTAACAATCGGTCCACAATGAACTCATTGTCAGTTCGAATATCA

        1|2
     S  E|V  N  L  Q  L  L  A  R  C  Y  L  S  N  S  Q  A  Y  S

                      2|3
    GCATATTATATCCTTAAAGGTTCAAAAACGCCTCAGTCTCGGTATTTATTTGCATTCTCA
241 ---------+---------+---------+---------+---------+---------+ 300
    CGTATAATATAGGAATTTCCAAGTTTTTGCGGAGTCAGAGCCATAAATAAACGTAAGAGT

                      2|3
     A  Y  Y  I  L  K|G  S  K  T  P  Q  S  R  Y  L  F  A  F  S

    TGCTTTAAGTTGGATCTTCTTGGAGAGGCTGAAGCTGCATTGTTGCCCTGTGAAGATTAT
301 ---------+---------+---------+---------+---------+---------+ 360
    ACGAAATTCAACCTAGAAGAACCTCTCCGACTTCGACGTAACAACGGGACACTTCTAATA

     C  F  K  L  D  L  L  G  E  A  E  A  A  L  L  P  C  E  D  Y

            3|4                                            4|5
    GCTGAAGAAGTTCCTGGTGGTGCAGCTGGGCATTATCTTCTTGGTCTTATATATATAGATAT
361 ---------+---------+---------+---------+---------+---------+ 420
    CGACTTCTTCAAGGACCACCACGTCGACCCGTAATAGAAGAACCAGAATATATATCTATA

            3|4                                             4|5
     A  E  E|V  P  G  G  A  A  G  H  Y  L  L  G  L  I  Y  R|Y
```

```
    TCTGGGAGGAAGAACTGTTCAATACAACAGTTTAGGATGGCATTGTCATTTGATCCATTG
421 ---------+---------+---------+---------+---------+---------+ 480
    AGACCCTCCTTCTTGACAAGTTATGTTGTCAAATCCTACCGTAACAGTAAACTAGGTAAC

    S  G  R  K  N  C  S  I  Q  Q  F  R  M  A  L  S  F  D  P  L
                                   5|6
    TGTTGGGAAGCATATGGAGAACTTTGTAGTTTAGGTGCCGCTGAAGAAGCCTCAACAGTT
481 ---------+---------+---------+---------+---------+---------+ 540
    ACAACCCTTCGTATACCTCTTGAAACATCAAATCCACGGCGACTTCTTCGGAGTTGTCAA
                                     5|6
    C  W  E  A  Y  G  E  L  C  S  L  G| A  A  E  E  A  S  T  V

    TTCGGGAATGTTGCTTCCCAGCGTCTTAAAACTTGTGTAGAACAAAGAATAAGCTTCTCA
541 ---------+---------+---------+---------+---------+---------+ 600
    AAGCCCTTACAACGAAGGGTCGCAGAATTTTGAACACATCTTGTTTCTTATTCGAAGAGT

    F  G  N  V  A  S  Q  R  L  K  T  C  V  E  Q  R  I  S  F  S

    GAAGGAGCAACCATAGACCAGATTACAGATTCTGATAAGGCCTTAAAAGATACAGGTTTA
601 ---------+---------+---------+---------+---------+---------+ 660
    CTTCCTCGTTGGTATCTGGTCTAATGTCTAAGACTATTCCGGAATTTTCTATGTCCAAAT

    E  G  A  T  I  D  Q  I  T  D  S  D  K  A  L  K  D  T  G  L

    TCGCAAACAGAACACATTCCAGGAGAGAACCAACAAGATCTGAAAATTATGCAGCAGCCT
661 ---------+---------+---------+---------+---------+---------+ 720
    AGCGTTTGTCTTGTGTAAGGTCCTCTCTTGGTTGTTCTAGACTTTTAATACGTCGTCGGA

    S  Q  T  E  H  I  P  G  E  N  Q  Q  D  L  K  I  M  Q  Q  P

    GGAGATATTCCACCAAATACTGACAGGCAACTTAGTACAAACGGATGGGACTTGAACACA
721 ---------+---------+---------+---------+---------+---------+ 780
    CCTCTATAAGGTGGTTTATGACTGTCCGTTGAATCATGTTTGCCTACCCTGAACTTGTGT

    G  D  I  P  P  N  T  D  R  Q  L  S  T  N  G  W  D  L  N  T
                         6|7
    CCTTCTCCAGTGCTTTTACAGGTAATGGATGCTCCACCGCCTCTGCTTCTTAAGAATATG
781 ---------+---------+---------+---------+---------+---------+ 840
    GGAAGAGGTCACGAAAATGTCCATTACCTACGAGGTGGCGGAGACGAAGAATTCTTATAC
                         6|7
    P  S  P  V  L  L  Q  V| M  D  A  P  P  P  L  L  L  K  N  M

    CGTCGTCCAGCAGTGGAAGGATCTTTGATGTCTGTACATGGAGTGCGTGTGCGTCGAAGA
841 ---------+---------+---------+---------+---------+---------+ 900
    GCAGCAGGTCGTCACCTTCCTAGAAACTACAGACATGTACCTCACGCACACGCAGCTTCT

    R  R  P  A  V  E  G  S  L  M  S  V  H  G  V  R  V  R  R  R
```

```
                                      7|8
     AACTTTTTTAGTGAAGAATTGTCAGCAGAGGCTCAAGAAGAATCTGGGCGCCGCCGTAGT
901  ---------+---------+---------+---------+---------+---------+ 960
     TTGAAAAAATCACTTCTTAACAGTCGTCTCCGAGTTCTTCTTAGACCCGCGGCGGCATCA
                                      7|8
      N  F  F  S  E  E  L  S  A  E| A  Q  E  E  S  G  R  R  R  S

     GCTAGAATAGCAGCAAGGAAAAAGAATCCTATGTCGCAGTCATTTGGAAAAGATTCCCAT
961  ---------+---------+---------+---------+---------+---------+ 1020
     CGATCTTATCGTCGTTCCTTTTTCTTAGGATACAGCGTCAGTAAACCTTTTCTAAGGGTA

      A  R  I  A  A  R  K  K  N  P  M  S  Q  S  F  G  K  D  S  H

     TGGTTACATCTTTCACCTTCCGAGTCAAACTATGCACCTTCTCTTTCCTCGATGATTGGA
1021 ---------+---------+---------+---------+---------+---------+ 1080
     ACCAATGTAGAAAGTGGAAGGCTCAGTTTGATACGTGGAAGAGAAAGGAGCTACTAACCT

      W  L  H  L  S  P  S  E  S  N  Y  A  P  S  L  S  S  M  I  G
                                   8|9
     AAATGCAGAATCCAAAGCAGCAAAGAAGCGATTCCTGATACCGTTACTCTAAATGATCCA
1081 ---------+---------+---------+---------+---------+---------+ 1140
     TTTACGTCTTAGGTTTCGTCGTTTCTTCGCTAAGGACTATGGCAATGAGATTTACTAGGT
                                   8|9
      K  C  R  I  Q  S  S  K  E  A| I  P  D  T  V  T  L  N  D  P

     GCAACGACGTCAGGCCAGTCTGTAAGTGACACTGGAAGCTCTGTTGATGATGAGGAAAAG
1141 ---------+---------+---------+---------+---------+---------+ 1200
     CGTTGCTGCAGTCCGGTCAGACATTCACTGTGACCTTCGAGACAACTACTACTCCTTTTC

      A  T  T  S  G  Q  S  V  S  D  T  G  S  S  V  D  D  E  E  K

     TCAAATCCTAGTGAATCTTCCCCGGATCGTTTCAGCCTTATTTCTGGAATTTCAGAAGTG
1201 ---------+---------+---------+---------+---------+---------+ 1260
     AGTTTAGGATCACTTAGAAGGGGCCTAGCAAAGTCGGAATAAAGACCTTAAAGTCTTCAC

      S  N  P  S  E  S  S  P  D  R  F  S  L  I  S  G  I  S  E  V
                                                               9|
     CTAGGCATTCTGAAAATTCTTGGAGATGGCCACAGGCATTTACATATGTACAAGTGTCAG
1261 ---------+---------+---------+---------+---------+---------+ 1320
     GATCCGTAAGACTTTTAAGAACCTCTACCGGTGTCCGTAAATGTATACATGTTCACAGTC
                                                               9|
      L  G  I  L  K  I  L  G  D  G  H  R  H  L  H  M  Y  K  C  Q|
```

Fig. 4 continued

```
      |10
      GAAGCTTTGTTGGCATATCAAAAGCTATCTCAGAAACAATACAATACACACTGGGTTCTC
1321  ---------+---------+---------+---------+---------+---------+ 1380
      CTTCGAAACAACCGTATAGTTTTCGATAGAGTCTTTGTTATGTTATGTGTGACCCAAGAG
      |10
      E  A  L  L  A  Y  Q  K  L  S  Q  K  Q  Y  N  T  H  W  V  L

           10|11
      ATGCAGGTTGGAAAAGCATATTTTGAGCTACAAGACTACTTCAACGCTGACTCTTCCTTT
1381  ---------+---------+---------+---------+---------+---------+ 1440
      TACGTCCAACCTTTTCGTATAAAACTCGATGTTCTGATGAAGTTGCGACTGAGAAGGAAA
        10|11
      M  Q| V  G  K  A  Y  F  E  L  Q  D  Y  F  N  A  D  S  S  F

      ACTCTTGCTCATCAAAAGTATCCTTATGCTTTGGAAGGAATGGATACATACTCCACTGTT
1441  ---------+---------+---------+---------+---------+---------+ 1500
      TGAGAACGAGTAGTTTTCATAGGAATACGAAACCTTCCTTACCTATGTATGAGGTGACAA

      T  L  A  H  Q  K  Y  P  Y  A  L  E  G  M  D  T  Y  S  T  V

          11|12
      CTTTATCACCTGAAAGAAGAGATGAGGTTGGGCTATCTGGCTCAGGAACTGATTTCAGTT
1501  ---------+---------+---------+---------+---------+---------+ 1560
      GAAATAGTGGACTTTCTTCTCTACTCCAACCCGATAGACCGAGTCCTTGACTAAAGTCAA
        11|12
      L  Y| H  L  K  E  E  M  R  L  G  Y  L  A  Q  E  L  I  S  V

                            12|13
      GATCGCCTGTCTCCAGAATCCTGGTGTGCAGTTGGGAACTGTTACAGTTTGCGTAAGGAT
1561  ---------+---------+---------+---------+---------+---------+ 1620
      CTAGCGGACAGAGGTCTTAGGACCACACGTCAACCCTTGACAATGTCAAACGCATTCCTA
                           12|13
      D  R  L  S  P  E  S  W| C  A  V  G  N  C  Y  S  L  R  K  D

      CATGATACTGCTCTCAAAATGTTTCAGAGAGCTATCCAACTGAATGAAAGATTCACATAT
1621  ---------+---------+---------+---------+---------+---------+ 1680
      GTACTATGACGAGAGTTTTACAAAGTCTCTCGATAGGTTGACTTACTTTCTAAGTGTATA

      H  D  T  A  L  K  M  F  Q  R  A  I  Q  L  N  E  R  F  T  Y

                           13|14
      GCACATACCCTTTGTGGCCACGAGTTTGCCGCATTGGAAGAATTCGAGGATGCAGAGAGA
1681  ---------+---------+---------+---------+---------+---------+ 1740
      CGTGTATGGGAAACACCGGTGCTCAAACGGCGTAACCTTCTTAAGCTCCTACGTCTCTCT
                          13|14
      A  H  T  L  C  G  H  E| F  A  A  L  E  E  F  E  D  A  E  R

      TGCTACCGGAAGGCTCTGGGCATAGATACGAGACACTATAATGCATGGTACGGTCTTGGA
1741  ---------+---------+---------+---------+---------+---------+ 1800
      ACGATGGCCTTCCGAGACCCGTATCTATGCTCTGTGATATTACGTACCATGCCAGAACCT

      C  Y  R  K  A  L  G  I  D  T  R  H  Y  N  A  W  Y  G  L  G
```

```
     ATGACCTATCTTCGTCAGGAGAAATTCGAGTTTGCGCAGCATCAATTTCAACTGGCTCTC
1801 ---------+---------+---------+---------+---------+---------+ 1860
     TACTGGATAGAAGCAGTCCTCTTTAAGCTCAAACGCGTCGTAGTTAAAGTTGACCGAGAG

      M  T  Y  L  R  Q  E  K  F  E  F  A  Q  H  Q  F  Q  L  A  L

     CAAATAAATCCAAGATCTTCAGTCATCATGTGTTACTATGGAATTGCTTTGCATGAGTCA
1861 ---------+---------+---------+---------+---------+---------+ 1920
     GTTTATTTAGGTTCTAGAAGTCAGTAGTACACAATGATACCTTAACGAAACGTACTCAGT

      Q  I  N  P  R  S  S  V  I  M  C  Y  Y  G  I  A  L  H  E  S
       14|15
     AAGAGAAACGATGAGGCGTTGATGATGATGGAGAAGGCTGTACTCACTGATGCAAAGAAT
1921 ---------+---------+---------+---------+---------+---------+ 1980
     TTCTCTTTGCTACTCCGCAACTACTACTACCTCTTCCGACATGAGTGACTACGTTTCTTA
      14|15
      K| R  N  D  E  A  L  M  M  M  E  K  A  V  L  T  D  A  K  N

     CCGCTCCCCAAGTACTACAAGGCTCACATATTAACCAGCCTAGGTGATTATCACAAAGCA
1981 ---------+---------+---------+---------+---------+---------+ 2040
     GGCGAGGGGTTCATGATGTTCCGAGTGTATAATTGGTCGGATCCACTAATAGTGTTTCGT

      P  L  P  K  Y  Y  K  A  H  I  L  T  S  L  G  D  Y  H  K  A

     CAGAAAGTTTTAGAAGAGCTCAAAGAATGTGCTCCTCAAGAAAGCAGTGTCCATGCATCG
2041 ---------+---------+---------+---------+---------+---------+ 2100
     GTCTTTCAAAATCTTCTCGAGTTTCTTACACGAGGAGTTCTTTCGTCACAGGTACGTAGC

      Q  K  V  L  E  E  L  K  E  C  A  P  Q  E  S  S  V  H  A  S

     CTTGGCAAAATATACAATCAGCTAAAGCAATACGACAAAGCCGTGTTACATTTCGGCATT
2101 ---------+---------+---------+---------+---------+---------+ 2160
     GAACCGTTTTATATGTTAGTCGATTTCGTTATGCTGTTTCGGCACAATGTAAAGCCGTAA

      L  G  K  I  Y  N  Q  L  K  Q  Y  D  K  A  V  L  H  F  G  I
                                                15|16
     GCTTTGGATTTAAGCCCTTCTCCATCTGATGCTGTCAAGATAAAGGCTTACATGGAGAGG
2161 ---------+---------+---------+---------+---------+---------+ 2220
     CGAAACCTAAATTCGGGAAGAGGTAGACTACGACAGTTCTATTTCCGAATGTACCTCTCC
                                                15|16
      A  L  D  L  S  P  S  P  S  D  A  V  K  I  K| A  Y  M  E  R
```

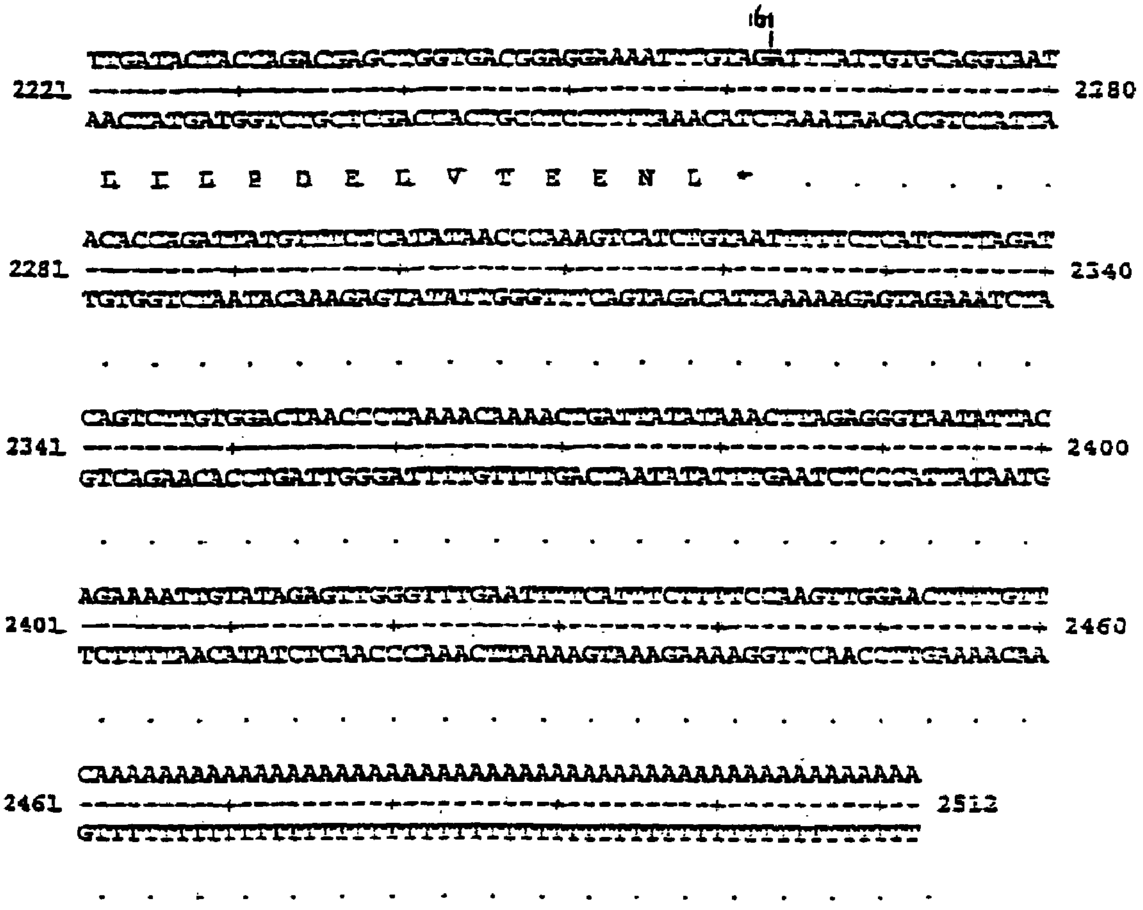

Fig. 4 continued

```
                                                            161
                                                             |
      TTGATACTACCAGACTAGCTGGTGACGGAGGAAAATTTGTAGATTTATTGTGCAGTAAT
2221  ------------+------------+------------+------------+------------+------------+  2280
      AACTATGATGGTCTGCTCGACCACTGCCTCCTTTAAACATCTAAATAACACGTCATTA

         L  I  L  P  D  E  L  V  T  E  E  N  L  *

      ACACCAGATTATGTTTCTCATATAACCCAAAGTCATCTGTAATTTTTCTCATCTTTAGAT
2281  ------------+------------+------------+------------+------------+------------+  2340
      TGTGGTCTAATACAAAGAGTATATTGGGTTTCAGTAGACATTAAAAGAGTAGAAATCTA

      CAGTCTTGTGGACTAACCCTAAAACAAAACTGATTATATAAACTTAGAGGGTAATATTAC
2341  ------------+------------+------------+------------+------------+------------+  2400
      GTCAGAACACCTGATTGGGATTTTGTTTTGACTAATATATTTGAATCTCCCATTATAATG

      AGAAAATTGTATAGAGTTGGGTTTGAATTTTCATTTCTTTTCCAAGTTGGACTTTTGTT
2401  ------------+------------+------------+------------+------------+------------+  2460
      TCTTTTAACATATCTCAACCCAAACTTAAAAGTAAAGAAAAGGTTCAACCTTGAAACAA

      CAAAAAAAAAAAAAAAAAAAAAAAAAAAAAAAAAAAAAAAAAAAAAAAAAAA
2461  ------------+------------+------------+------------+------------+--  2512
      GTTTTTTTTTTTTTTTTTTTTTTTTTTTTTTTTTTTTTTTTTTTTTTTTTTT
```

CDC27B Gene Structure

```
                                                          SEQ ID NO 6
Cdc27A1    1- MMENLLANCVQKNLNHFMFTNAIFLCELLLAQFPSEVNLQLLARCYLSNS
Cdc27B     1- MEAMLV-DCVNNSLRHFVYKNAIFMCERLCAEFPSEVNLQLLATSYLQNN
                                 SEQ ID NO 10

   SEQ ID NO 6
Cdc27A1   51- QAYSAYYILKGSKTPQSRYLFAFSCFKLDLLGEAEAALLP-CEDYAEEVP
Cdc27B    50- QAYSAYHLLKGTQMAQSRYLFALSCFQMDLLNEAESALCPVNEPGAE-IP
                                 SEQ ID NO 10

Cdc27A1  100- GGAAGHYLLGLIYRYSGRKNCSIQQFRMALSFDPLCWEAYGELCSLGAAE
Cdc27B    99- NGAAGHYLLGLIY----KKNAA-QQFKQSLTIDPLLWAAYEELCILGAAE
                                 SEQ ID NO 10

Cdc27A1  150- EASTVFGNVASQRLQKTCVEQRISFSEG-ATIDQ--ITDSDKAL--KDTG
Cdc27B   144- EATAVFGETAALSIQKQYMQQ-LSTSLGLNTYNEERNSTSTKNTSSEDYS
                 SEQ ID NO 10

Cdc27A1  194- LSQTEHIPGENQQDLKIMQQPGDIPPNTDRQLSTNGWDLNTPSPVLLQVM
Cdc27B   193- PRQSKHTQSHGLKDISGNFHSHGVNGGV----SNMSFY-NTPSPVAAQLS

Cdc27A1  244- D-APPPLLL NMRRPAV-EG-SLMS-------VHG-VRVRRRNFFSE---
Cdc27B   238- GIAPPPL-FRNFQ-PAVANPNSLITDSSPKSTVNSTLQAPRRKFVDEGKL

Cdc27A1  280- -ELSAEAQEESG-RRRSARIAA-------RKKNPMSQSFGKDSHWLHLSP
Cdc27B   286- RKISGRLFSDSGPRR-SSRLSADSGANINSSVATVSGNVNNASKYLGGSK

                                                   SEQ ID NO 12
Cdc27A1  321- SESNYAPSLSSMIGKCRIQSSK------EAIPD-TV--------TLNDPA
Cdc27B   335- --------LSSLALRS-VTLRKGHSWANENM-DEGVRGEPFDDSRPNTAS

Cdc27A1  356- TTSGQSVSDTGSSVDDEEKSNPSE--SSPDRFSLIS-GISEVLSILKILG
Cdc27B   375- TTGSMASND----QEDETMSIGGIAMSSQT----ITIGVSEILNLLRTLG

Cdc27A1  403- DGHRHLHMYKCQEALLAYQKLSQKQYNTHWVLMQVGKAYFELQDYFNADS
Cdc27B   417- EGCRLSYMYRCQEALDTYMKLPHKHYNTGWVLSQVGKAYFELIDYLEAEK

Cdc27A1  453- SFTLAHQKYPYALEGMDTYSTVLYHLKEEMRLGYLAQELISVDRLSPESW
Cdc27B   467- AFRLARLASPYCLEGMDIYSTVLYHLKEDMKLSYLAQELISTDRLAPQSW

Cdc27A1  503- CAVGNCYSLRKDHDTALKMFQRAIQLNERFTYAHTLCGHEFAALEEFEDA
Cdc27B   517- CAMGNCYSLQKDHETALKNFLRAVQLNPRFAYAHTLCGHEYTTLEDFENG

Cdc27A1  553- ERCYRKALGIDTRHYNAWYGLGMTYLRQEKFEFAQHQFQLALQINPRSSV
Cdc27B   567- MKSYQNALRVDTRHYNAWYGLGMIYLRQEKLEFSEHHFRMAFLINPSSSV

Cdc27A1  603- IMCYYGIALHESKRNDEALMMMEKAVLTDAKNPLPKYYKAHILTSLGDYH
Cdc27B   617- IMSYLGTSLHALKRSEEALEIMEQAIVADRKNPLPMYQKANILVCLERLD

Cdc27A1  653- KAQKVLEELKECAPQESSVHASL-GKIYNQLKQYDKAVLHFGIALDLSPS
Cdc27B   667- EALEVLEELKEYAPSESSVYA-LMGRIYKRRNMHDKAMLHFGLALDMKPP

                     SEQ ID NO 7
Cdc27A1  702- PSDAVKIKAYMERLILPDELVTEENL
Cdc27B   716- ATDVAAIKAAMEKLHVPDEIDESP
```

FIGURE 6

METHOD OF INCREASING YIELD IN PLANTS

CROSS REFERENCE TO RELATED APPLICATIONS

This application is a Divisional of U.S. application Ser. No. 10/036,492, filed Jan. 7, 2002, abandoned, which is a Continuation of PCT/EP00/06401, filed Jul. 5, 2000.

FIELD OF THE INVENTION

The present invention relates to at least partially purified protein, capable of modulating the DNA replication in plants, muteins thereof, DNA coding therefor and to a method to confer to one or more plant cells the capacity to provide such a protein or mutein. The invention also relates to plants, comprising the said DNA and the progeny thereof.

BACKGROUND OF THE INVENTION

The regulation of the cell cycle in plants is poorly understood. Most of the knowledge regarding the regulation of DNA replication, also known as the S-phase of the cell cycle regulation originates from experimental data obtained in yeast and mammalian cells. However, the importance to understand the cell cycle regulation in plant cells has become increasingly important in agriculture, e.g. to control growth of plants at stress conditions, to obtain resistance against parasites that block or modulate the cell cycle regulation, or to improve the yield of agriculturally important crops. Further, one might be interested to intervene in the cell cycle regulation by allowing further rounds of DNA replication, but simultaneously preventing further cell cycle progress by blocking the subsequent mitosis. In this way, cells may be obtained having multiple sets of their genetic material, so that plants with a high rate of endoreduplication may be generated. The term "endoreduplication" means recurrent DNA replication without consequent mitosis and cytokinesis.

From experiments in yeast, it is known that DNA replication and mitosis are coupled events in the cell cycle. Paulovich et al., 1997; Cell 88, 315-321. Genetic studies in yeast for example suggest that the CDC7 serine-threonine kinase plays a role in the initiation of DNA synthesis. Evidence has been presented that CDC7 is apparently directly involved in the activation of individual early—as well as late replication origins during S-phase (Bousset and Diffley, 1998, Genes Dev 12, 480-490; Donaldson et al., 1998, Genes Dev 12, 491-501). The protein levels of CDC7 are constant during the cell cycle.

Activation of CDC7 as a kinase occurs at the G1/S transition of the cell cycle and is dependent on the binding with another factor, DBF4, at the G1/S transition of the cell cycle, probably by phosphorylating proteins at the origins (Kitada et al, 1992; Genetics 131: 21-29, Lei et al; Genes and Development 11, 3365-3374, 1997). In order to function as a kinase, the CDC7 kinase may be a substrate for one or more phosphorylation events. Overexpressed kinase-negative mutants of CDC7 arrest yeast cells in the G1 to S transition and inhibit growth. Further experiments showed that the inactivation of wild-type CDC7 function probably can be explained through titration of DBF4 by the inactive cdc7 mutant proteins (Ohtoshi et al., 1997, Mol Gen Genet 254, 562-570). In addition to mechanisms to control the onset of DNA replication, other mechanisms contribute to restrict DNA replication to occur only once during the cell cycle. For example, the CDC16, CDC23 and CDC27 proteins are part of a high molecular weight complex, known as the anaphase promoting complex (APC) or cyclosome, (see Romanowski and Madine, Trends in Cell Biology 6, 184-188, 1996, and Wuarin and Nurse, Cell 85, 785-787 (1996), both incorporated herein by reference). The complex in yeast is composed of at least 8 proteins, the TPR (tetratricopeptide repeat) containing proteins CDC16, CDC23 and CDC27, and five other subunits named APC1, APC2, APC4, APC5 and APC7 (Peters et al. 1996, Science 274, 1199-1201). The APC targets its substrates for proteolytic degradation by catalyzing the ligation of ubiquitin molecules to these substrates. APC-dependent proteolysis is required for the separation of the sister chromatids at meta—to anaphase transition and for the final exit from mitosis. Among the APC-substrates are the anaphase inhibitor protein Pds1p and mitotic cyclins such as cyclin B, respectively (Ciosk et al. 1998, Cell 93, 1067-1076; Cohen-Fix et al. 1996, Genes Dev 10, 3081-3093; Sudakin et al. 1995, Mol Biol Cell 6, 185-198; Jorgensen et al. 1998, Mol Cell Biol 18, 468-476; Townsley and Ruderman 1998, Trends Cell Biol 8, 238-244). To become active as a ubiquitin-ligase, at least CDC16, CDC23 and CDC27 need to be phosphorylated in the M-phase (Ollendorf and Donoghue 1997, J Biol Chem 272, 32011-32018). Activated APC persists throughout Gl of the subsequent cell cycle to prevent premature appearance of B-type cyclins which would result in an uncontrolled entry into S-phase (Irniger and Nasmyth 1997, J Cell Sci 110, 1523-1531). It has been demonstrated in yeast that mutations in either of at least two of the APC components, CDC16 and CDC27, can result in DNA overreplication without intervening passages through M-phases (Heichman and Roberts 1996, Cell 85, 39-48). CDC16, CDC23 and CDC27 all are tetratricopeptide repeat (TPR) containing proteins. A suggested minimal consensus sequence of the TPR motif is as follows: $X_3$—W—$X_2$-L-G-$X_2$—Y—$X_8$-A-$X_3$—F—$X_2$-A-$X_4$—P—$X_2$ (Lamb et al. 1994, EMBO J 13, 4321-4328; X denotes any amino acid, $X_n$ a stretch of n of such amino acids). However, the consensus residues can exhibit significant degeneracy and little or no homology is present in non-consensus residues. The hydrophobicity and size of the consensus residues, rather than their identity, seems to be important. TPR motifs are present in a wide variety of proteins functional in yeast and higher eukaryotes in mitosis (including the APC protein components CDC16, CDC23 and CDC27), transcription, splicing, protein import and neurogenesis (Goebl and Yanagida 1991, Trends Biochem Sci 16, 173-177). The TPR forms a α helical structure, tandem repeats organize into a superhelical structure ideally suited as interfaces for protein recognition (Groves and Barford 1999, Curr Opin Struct Biol 9, 383-389). Within the α helix, two amphipathic domains are usually present, one at the $NH_2$-terminus and the other near the COOH-terminus (Sikorski et al. 1990, Cell 60, 307-317).

SUMMARY OF THE INVENTION

In order to understand the mechanisms playing a role in plant cell cycle regulation, in particular the DNA replication, and to understand endoreduplication in plants, the present inventors isolated several novel plant DNA sequences, coding for novel proteins, or novel amino acid sequences thereof involved in the modulation of DNA replication, using degenerated PCR primers based on known genomic or cDNA sequences, e.g. of yeast, mammals and insects.

"Capable of modulating the DNA replication in plants" is to be understood as the capacity of a protein to alter the natural DNA replication mechanism in the said plant, e.g. by up- or down-regulation of the DNA replication in a way, different from the natural situation, or to a higher or lower extent with respect to the natural situation. The natural situation is to be understood as the situation wherein DNA replication takes place in plants, in which the DNA replication machinery is not affected by the introduction of foreign genetic material. Such altering includes mediating e.g. the onset of DNA replication, the rate and extent of DNA replication, the timing of DNA replication in the cell cycle, coupling or uncoupling DNA replication with/from actual subsequent cell division etcetera.

Proteins

By using degenerated oligonucleotides as amplification primers, based on conserved sequence regions of the CDC7 homologue gene of *Saccharomyces cerevisiae* and *Schizosaccharomyces pombe* and on conserved sequence regions of the CDC27 homologue genes of *Schizosaccharomyces pombe* and from *Aspergillus Nidulans*, drosophila and human, the present inventors surprisingly found such novel proteins and amino acid sequences. Reference is made to the examples.

Thus, novel cDNAs and proteins comprising one or more novel amino acid sequences were found. The present invention therefore relates in the first place to an at least partially purified protein, capable of modulating DNA replication in plants, at least comprising in the amino acid sequence a) one or more of the amino acid sequences chosen from the group consisting of those, given by SEQ ID NOS 2, 3 and 4, b) one or more of the amino acid sequences chosen from the group consisting of those, given by SEQ ID NOS 6, 7, 10 and 12.

c) one or more amino acid sequences having at least 50% amino acid identity with those of a), or d) one or more amino acid sequences having at least 50% amino acid identity with those of b).

By using degenerated CDC7 oligonucleotides to amplify a PCR fragment as is indicated above and will be further detailed in the examples, a novel *Arabidopsis* cDNA comprising coding sequence of an novel *Arabidopsis* CDC7 homologue gene was found (SEQ ID NO 8). By comparison of the said sequences with sequences of the EMBL and EMBLnew databanks, a genomic *Arabidopsis thaliana* sequence was found (accession number Z97342). In this known genomic sequence however, only 11 exons were identified. The novel DNA according to the present invention however clearly indicated the presence of 3 additional coding sequences coding for novel amino acid sequences (SEQ ID NO 2, 3, 4) being part of a DNA replication modulating plant protein, homologous to yeast CDC7.

The novel amino acid sequence SEQ ID No 2 (GYGIVYKATRKTDGTEFAIK) is located in two highly conserved domains in protein kinases, Domain I and II (Hawks et al., 1988, Science 241, 42-52). The sequence GYGIV is part of the nucleotide (ATP) binding domain, also known as Domain I in protein kinases. Domain I is part of the catalytic domain of protein kinases. The Glycines (G) are believed to form an elbow around the nucleotide, and the Valine (V) is believed to contribute to positioning of the Glycines. The first Glycine and the Valine are invariant in all protein kinases. The second Glycine is almost invariant.

The sequence AIK in the same peptide is also highly conserved and it is located in Domain II, which is also part of the catalytic domain. The Alanine (A) and the Lysine (K) are invariant in all kinases, and the Isoleucine is highly conserved. The Lysine residue appears to be involved in mediating the phosphotransfer reaction (Hawks et al, 1988).

This exon is responsible for the kinase activity of CDC7. This implies that the CDC7 coding sequence from the state of the art is not functional.

The novel exon encoded by amino acid sequence SEQ ID No 3 (DVIEKKDGPCSGTKGFRAPE) is part of Domain VIII of protein kinases. Mutagenesis has implicated a role of this domain in the catalytic activity (Hawks et al., 1988). In the sequence TKGFRAPE, the amino acids Threonine (T), Phenylalanine and Alanine (A) are highly conserved, and the Glutamic Acid (E) is invariant. Moreover, substitution of the corresponding threonine in the yeast CDC7 homologue (position 281 of the yeast CDC7; position 722 in SEQ ID No 1) to a glutamate resulted in a dominant-negative CDC7mutant (Ohtoshi et al. 1997, Mol Gen Genet 254, 562-570).

The novel exon, encoded by amino acid sequences SEQ ID No 4 (NIKDIAQLRGSEELWEVAKLHNRESSFPK) is located in Domain XI of protein kinases, and that in the peptide, the first Leucine (L), and the second Lysine (K) are highly conserved and therefore are believed to be quite important for the correct activity of the protein.

In addition, using degenerated CDC27 oligonucleotides, an *Arabidopsis thaliana* cDNA sequence termed CDC27A1 was found, which upon comparison in the above mentioned databanks, showed high homology with an *Arabidopsis thaliana* genomic DNA sequence (accession number AC 001645). Again, the coding sequence of CDC27A1 (SEQ ID NO 9), found by the present inventors, indicated the presence of two additional coding regions in the *Arabidopsis* CDC27, the gene, corresponding with the amino acid sequences given by SEQ ID NOS 6 and 7. Thus, novel DNA replication modulating proteins in plants were found, comprising one or more of the above mentioned novel amino acid sequences.

The novel exon encoded by amino acid sequence SEQ ID No 6 (VNLQLLARCYLSNQAYSAYYILK) is part of a unique $NH_2$-terminal domain conserved in CDC27 homologues of different origin. The unique domain is located upstream of the $NH_2$-terminal TPR unit of CDC27 (Tugendreich et al. 1993, Proc Natl Acad Sci USA 90, 10031-10035). The role of this domain is currently not known, but its conservation suggests that it is indispensable for CDC27 function. The $NH_2$-terminal TPR of CDC27 is not tandemly repeated and spans the amino acid residues 174 to 202 in SEQ ID No 5. Proteins, comprising this novel exon sequence according to the invention may therefore promote APC-substrate action and therewith allowing DNA-replication. On the other hand, a peptide comprising the novel exon sequence may be used to occupy the binding region of the substrates for the APC complex, and therewith inhibiting the complex-substrate interactions, resulting in inactivation of APC and to polyploiddization/endoreduplication.

The novel amino acid sequence SEQ ID No 7 (AYMERLILPDELVTEENL) is located just after the last (10th) TPR of CDC27 spanning the amino acid residues 670-703 in SEQ ID No 5. Carboxy-terminal extensions downstream from this $10^{th}$ TPR and variable in length and sequence are common in all known CDC27 proteins. However, the sequence SEQ ID No 7 shows 50 and 55% homology to the corresponding regions of the CDC27 homologues of *Schizosaccaromyces pombe* and *Aspergillus nidulans*, respectively. Moreover, and previously not recognized, the 25 carboxy-terminal amino acids (ending with SEQ ID No 7) immediately downstream of the $10^{th}$ TPR compose aids exists in the SKI3 antiviral protein of *Saccharomyces cerevisiae* (Rhee et al. 1989, Yeast 5, 149-158). Remarkably, three consecutive core amino acids of this TPR, RLI, are also present in SEQ ID No 7 and, although very limited, some further homology can be discovered. Thus, although circumstancial, these data may suggest that SEQ ID No 7 is part of a truncated TPR. If so, the block of tandemly repeated TPRs in CDC27 should be extended from 9 (spanning amino acids 406 to 703 in SEQ ID No 5) to 10 (amino acids 704 to 728 in SEQ ID No 5). Interestingly, it has been suggested that a dimer of the basic 34 amino acid TPR repeat is the more common evolutionary unit (Sikorski et al. 1990, Cell 60, 307-317).

By analyzing patterns of CDC27A1 expression, the present inventors furthermore identified the existence of a second isoform of the CDC27A1 gene. Said isoform, termed CDC27A2 is characterized in that a fragment of 33 nucleotides present in CDC27A1 (nucleotides 1029-1061 of SEQ ID NO 9) is missing in CDC27A2. The nucleotide sequence of the CDC27A2 cDNA is given in SEQ ID NO 14, the corresponding amino acid sequence of the CDC27A2 protein is defined in SEQ ID NO 11. SEQ ID NO 11 is different from SEQ ID NO 5 in that the amino acid sequence 'AIPDTVTLNDP' (SEQ ID NO 12) present in CDC27A1 is absent in CDC27A2.

Another CDC27-like gene from *Arabidopsis thaliana* was identified by the present inventors via in silico cloning. The gene, termed CDC27B has GenBank accession number AC006081 and is annotated as CDC27. However, upon isolation and characterization of the corresponding cDNA, the present inventors noticed that the amino acid sequence predicted and presented in GenBank is lacking the stretch of 161 $NH_2$-terminal amino acids as given in SEQ ID NO 10.

The cDNA sequence of CDC27B is defined in SEQ ID NO 15 and the derived amino acid sequence of the CDC27B protein is given in SEQ ID NO 13. The full-length CDC27B protein comprises a peptide 75% identical to the peptide as defined in SEQ ID NO 6. As discussed supra, SEQ ID NO 6, and thus also SEQ ID NO 10, are part of a unique $NH_2$-terminal domain conserved in CDC27 homologues of different origin.

The effect of mutations in one out of the tandem series of TPRs can be very specific. For instance, a point mutation in the most highly conserved $7^{th}$ TPR domain of yeast CDC27 results in a greatly reduced affinity for interaction with yeast CDC23, but not for interaction with yeast CDC16 or wild-type CDC27. A single amino acid insertion in the same domain destroys the α-helix and abolishes interaction with wild-type CDC27 as well as CDC16 (Lamb et al. 1994, EMBO J 13, 4321-4328). Moreover, detailed experiments with the human TPR-containing CDC16 and CDC27 homologues and another TPR-containing protein regulating the APC-activity, PP5, revealed that TPR proteins display discriminate binding to other TPR proteins. More specifically for CDC27, deletion of the first TPR domain in this protein abolishes CDC16 binding, but not PP5 binding (Ollendorf and Donoghue 1997, J Biol Chem 272, 32011-32018). Mutagenesis studies with the yeast CDC23 showed that only a few residues in or near the most canonical $6^{th}$ TPR unit result in temperature-sensitive defects (Sikorski et al. 1993, Mol Cell Biol 13, 1212-1221). Separate TPR domains thus seem to be involved in specific interactions with other proteins and only very limited alterations in these domains seem to be tolerated.

Any erroneous modulation of APC activity, e.g. by mutations in SEQ ID No 6 as part of a conserved sequence in CDC27 proteins and/or SEQ ID No 7 being a putative novel truncated TPR motif in CDC27, will likely result in loss of control over normal DNA replication cycles via the mechanisms described above. Mutations in CDC27 can indeed trigger DNA overreplication and thus the generation of polyploid cells (Heichmann and Roberts 1996, Cell 85, 39-48). Such endoreduplication might be related to cell expansion (Traas et al. 1998, Curr Opin Plant Biol 1, 498-503) and, thus, a higher storage capacity in such polyploid cells. This advantageous property is highly desired in crop plants or parts of plants such as seeds, roots, tubers and fruits.

Modulating the said amino acid sequence would impair the formation of functional APC, whereas cdc27 comprising such a mutation would still be able to interact with the substrate and therewith titrating the substrate out, leading to the abolishment of APC-function in the plant cell, resulting in polyploid cells.

It is to be understood, that DNA replication modulating proteins according to the present invention, comprising one or more of the above mentioned amino acid sequences, or having 80% amino acid identity therewith, may originate from plant species as well as from other species as long as the said proteins are capable of modulating DNA replication in one or more plant species.

The term "protein" is to be understood as any amino acid sequence having a biological function, optionally modified by e.g. glycosylation. The protein according to the present invention preferably comprises one or more of the amino acid sequences according to c) or d), the respective amino acid identity preferably being at least 50%

The term "protein" includes single-chain polypeptide molecules as well as multiple-polypeptide complexes where individual constituent polypeptides are linked by covalent or non-covalent means. The term "polypeptide" includes peptides of two or more amino acids in length, typically having more than 5, 10 or 20 amino acids.

It will be understood that amino acid sequences of the invention are not limited to the sequences obtained from the particular protein but also include homologous sequences obtained from any source, for example related plant proteins, cellular homologues and synthetic peptides, as well as variants or derivatives thereof.

Thus, the present invention covers variants, homologues or derivatives of the amino acid sequences of the present invention, as well as variants, homologues or derivatives of the nucleotide sequence coding for the amino acid sequences of the present invention.

In the context of the present invention, a homologous sequence is taken to include an amino acid sequence which is at least 50, 60, 70, 80 or 90% identical, preferably at least 95 or 98% identical at the amino acid level over at least 18, preferably all amino acids within the sequences as shown in SEQ ID Nos 2, 3, 4, 6 and 7 in the sequence listing herein. In particular, homology should typically be considered with respect to those regions of the sequence known to be essential for the above discussed functions of the novel amino acid sequences rather than non-essential neighbouring sequences. Although homology can also be considered in terms of similarity (i.e. amino acid residues having similar chemical properties/ functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% Homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is -12 for a gap and -4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see http://www.ncbi.nih.gov/BLAST/), FASTA (Atschul et al., 1990, J. Mol. Biol., 403-410; FASTA is available for online searching at, for example, http://www.2.ebi.ac.uk.fasta3) and the GENEWORKS suite of comparison tools. However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

Polypeptide Variants and Derivatives

The terms "variant" or "derivative" in relation to the amino acid sequences of the present invention includes any substitution of, variation of, modification of, replacement of, deletion of or addition of one (or more) amino acids from or to the sequence providing the resultant amino acid sequence has similar activity as the polypeptides presented in the sequence listings.

The sequences of the invention may be modified for use in the present invention. Typically, modifications are made that maintain the activity of the sequence. Amino acid substitutions may be made, for example from 1, 2 or 3 to 10, 20 or 30 substitutions provided that the modified sequence retains the relevant activity. E.g. the kinase activity should be maintained in such a variant of a peptide according to the invention comprising SEQ ID NO 2. Amino acid substitutions may include the use of non-naturally occurring analogues, for example to increase blood plasma half-life of a therapeutically administered polypeptide.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Proteins of the invention are typically made by recombinant means. However they may also be made by synthetic means using techniques well known to skilled persons such as solid phase synthesis. Proteins of the invention may also be produced as fusion proteins, for example to aid in extraction and purification. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the function of the protein of interest sequence.

Proteins of the invention may be in a substantially isolated form. It will be understood that the protein may be mixed with carriers or diluents which will not interfere with the intended purpose of the protein and still be regarded as substantially isolated. A protein of the invention may also be in a substantially purified form, in which case it will generally comprise the protein in a preparation in which more than 90%, e.g. 95%, 98% or 99% of the protein in the preparation is a protein of the invention.

In a special embodiment, the protein according to the present invention comprises the amino acid sequence as given in SEQ ID NO 1 or NO 5 or NO 11 or NO 13, or has at least 50%, preferably at least 60%, more preferably at least 70, still more preferably 80% and most preferably at least 90% amino acid identity with one of the said sequences. SEQ ID NO 1 relates to the complete amino acid sequence (889 AA) of the novel CDC7 protein according to the present invention comprising SEQ ID NOS 2, 3 and 4 (AA 411-430, 710-729, 767-795). SEQ ID NO 5 is the complete amino acid sequence (727 AA) of the novel plant CDC27A1 comprising SEQ ID NOS 6 and 7 and 12 (AA 37-60 and AA 711-727 and AA 344-354 respectively). SEQ ID NO 11 is the complete amino acid sequence (716 AA) of the novel plant CDC27A2 comprising SEQ ID NOS 6 and 7 (AA 37-60 and AA 700-716, respectively) but lacking SEQ ID NO 12.

SEQ ID NO 13 is the complete amino acid sequence (739 AA) of the novel plant CDC27B comprising SEQ ID NO 10 (AA-1-161) which itself comprises a peptide 75% identical to SEQ ID NO 6 (AA 36-59).

Although the proteins according to the present invention may be of non-plant origin, as is indicated above, the protein according to the present invention is preferably a plant protein, more preferably a CDC7 or CDC27 protein, or a functional analogue thereof. A functional analogue is to be understood as any protein or peptide having similar biological effects as a plant CDC7 protein or a CDC27 protein, irrespectively of the origin thereof.

Mutein

In another embodiment, the present invention relates to a mutein of the protein according to the present invention, said mutein comprising at least one amino acid substitution, deletion or addition, affecting the DNA replicative effect of the said protein.

As is already indicated above, the proteins according to the present invention are of high interest for an improvement of e.g. agricultural crops or parasite resistance. By substituting, deleting or adding amino acids to the protein according to the present invention, the modulating effect thereof can be affected, which may lead to desirable or improved properties of the protein.

In particular, DNA replication modulating proteins according to the invention may be activated or deions or additions may be situated within or flanking the amino acid sequence, as given by SEQ ID NOS 2, 3, 4, 6, 7, 10 or 12 (or having at least 50% amino acid identity therewith).

DNA replicating modulating proteins according to the invention may also comprise one or more tetratricopeptide repeat (TPR) domains. Such domains have been identified in CDC27 (amino acid regions 174-202, 403-431, 432-465, 466-499, 500-533, 534-567, 568-601, 602-635, 636-669, 670-703 in SEQ ID No 5; delineation of regions based on the yeast CDC27 homologue; Lamb et al. 1994, EMBO J 13, 4321-4328) as well as in CDC16, CDC23 and many other proteins (Goebl and Yanagida 1991, Trends Biochem Sci 16, 173-177). The function of these TPR domains is to enable the protein to interact with other proteins in the anaphase promoting complex (APC). In the CDC27 protein according to the present invention, a novel TPR or TPR-like domain has been identified which includes SEQ ID No 7. Mutation analysis in TPR domains of yeast CDC27 has revealed that intact TPRs are necessary for CDC27 function (Lamb et al. 1984, EMBO J 13, 4321-4328) and, thus, also for a functional APC. In the absence of CDC27 function, DNA synthesis becomes uncoupled from cell cycle progression resulting in the establishment of polyploid cells (Heichman and Roberts 1996, Cell 85, 39-48).

Peptides

Further, the present invention relates to a peptide, comprising a) one or more of the amino acid sequences chosen from the group consisting of those given by SEQ ID NOS 2, 3 and 4, b) one or more of the amino acid sequences chosen from the group consisting of those, given by SEQ ID NOS 6 and 7, c) one or more amino acid sequences having at least 50% amino acid identity with those of a), or d) one or more amino acid sequences having at least 50% amino acid identity with those of b).

These peptides, firstly identified by the present inventors, are or maybe part of important regulatory sites for binding cellular factors or being a substrate for activating/deactivating mechanisms, such as phosphorylation.

Antibodies

Furthermore, the present invention relates to antibodies specifically recognizing a cell cycle interacting protein according to the invention or parts, i.e. specific fragments or epitopes, of such a protein. The antibodies of the invention can be used to identify and isolate other cell cycle interacting proteins and genes in any organism, preferably plants. These antibodies can be monoclonal antibodies, polyclonal antibodies or synthetic antibodies as well as fragments of antibodies, such as Fab, Fv or scFv fragments etc. Monoclonal antibodies can be prepared, for example, by the techniques as originally described in Köhler and Milstein, Nature 256 (1975), 495, and Galfré, J. Meth. Enzymol. 73 (1981), 3, which comprise the fusion of mouse myeloma cells to spleen cells derived from immunized mammals. Furthermore, antibodies or fragments thereof to the aforementioned peptides can be obtained by using methods which are described, e.g., in Harlow and Lane “Antibodies, A Laboratory Manual”, CSH Press, Cold Spring Harbor, 1988. These antibodies can be used, for example, for the immunoprecipitation and immunolocalization of proteins according to the invention as well as for the monitoring of the synthesis of such proteins, for example, in recombinant organisms, and for the identification of compounds interacting with the protein according to the invention. For example, surface plasmon resonance as employed in the BIAcore system can be used to increase the efficiency of phage antibodies selections, yielding a high increment of affinity from a single library of phage antibodies which bind to an epitope of the protein of the invention (Schier, Human Antibodies Hybridomas 7 (1996), 97-105; Malmborg, J. Immunol. Methods 183 (1995), 7-13). In many cases, the binding phenomena of antibodies to antigens is equivalent to other ligand/anti-ligand binding.

DNA Sequences

Further, the present invention relates to a non-genomic DNA sequence, coding for a protein or mutein or peptide according to the present invention, or a DNA sequence having a sequence homology of at least 75% with the said sequence, or to the complementary sequence thereof. Also DNA sequences having at least 75% homology with the above mentioned DNA sequences are encompassed within the invention. These sequences are particularly useful in the generation of DNA vectors to multiply the DNA sequence or to introduce the said sequence in a host organism, in order to obtain the encoded protein. Further said sequences or parts thereof are advantageously used to identify and isolate homologous sequences from other biological species.

The DNA sequence is preferably substantially free of sequences intervening the coding sequence, and is preferably cDNA.

DNA-sequences of the invention comprise nucleic acid sequences encoding the amino acid sequences of the invention. It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

Polynucleotides of the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or life span of polynucleotides of the invention.

The terms “variant”, “homologue” or “derivative” in relation to the nucleotide sequence of the present invention include any substitution of, variation of, modification of, replacement of, deletion of or addition of one (or more) nucleic acid from or to the sequence providing the resultant nucleotide sequence codes for a polypeptide, preferably having at least the same activity as sequences presented in the sequence listings.

As indicated above, with respect to sequence homology, preferably there is at least 75%, more preferably at least 85%, more preferably at least 90% homology to the sequences shown in the sequence listing herein. More preferably there is at least 95%, more preferably at least 98%, homology. Nucleotide homology comparisons may be conducted as described above. A preferred sequence comparison program is the GCG Winsconsin Bestfit program described above. The default scoring matrix has a match value of 10 for each identical nucleotide and −9 for each mismatch. The default gap creation penalty is −50 and the default gap extension penalty is −3 for each nucleotide.

The present invention also encompasses nucleotide sequences that are capable of hybridising selectively to the sequences presented herein, or any variant, fragment or derivative thereof, or to the complement of any of the above. Nucleotide sequences are preferably at least 15 nucleotides in length, more preferably at least 20, 30, 40 or 50 nucleotides in length.

The term "hybridization" as used herein shall include "the process by which a strand of nucleic acid joins with a complementary strand through base pairing" as well as the process of amplification as carried out in polymerase chain reaction technologies.

30, for instance at least 40, 60 or 100 or more contiguous nucleotides. Preferred polynucleotides of the invention will comprise regions preferably at least 80 or 90% and more preferably at least 95% homologous to nucleotides (1229-1291), (2126-2187) or (2298-2385) of SEQ ID No 8 or (109-181) or (2125-2181) or (1029-1061) of SEQ ID No 9; or (109-181) or (2092-2148) of SEQ ID NO 14; or (1-483) of SEQ ID NO 15.

Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

In a preferred aspect, the present invention covers nucleotide sequences that can hybridise to the nucleotide sequence of the present invention under stringent conditions (e.g. 65° C. and 0.1×SSC {1×SSC=0.15 M NaCl, 0.015 M $Na_3$ Citrate pH 7.0).

Where the polynucleotide of the invention is double-stranded, both strands of the duplex, either individually or in combination, are encompassed by the present invention. Where the polynucleotide is single-stranded, it is to be understood that the complementary sequence of that polynucleotide is also included within the scope of the present invention.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in plant cells, may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of SEQ ID Nos 8 or 9 or 14 or 15. This may be useful where for example under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences, such as SEQ ID No 8 or 9. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as a DNA polynucleotides and probes according to the invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

For expression of the DNA sequence according to the invention it may in some instances be advantageous to incorporate one or more intervening sequences (introns) in the sequence coding for the protein to be expressed, as in some expression systems, one or more splicing events must take place in order to obtain high expression rates (e.g. for expression of a barley thionin in transgenic tobacco; Carmona et al. 1993, Plant J 3, 457-462).

However, in most cases, the coding sequence (i.e. the cDNA), accompanied by the proper regulatory elements, such as promotor and terminator sequences, are sufficient for proper expression.

In a special embodiment (referring to FIGS. 1 and 2), the invention relates to a cDNA sequence, comprising the DNA sequence as given by SEQ ID NO 8 or SEQ ID NO 9 or SEQ ID NO 14 or SEQ ID NO 15, or having a sequence homology with SEQ ID NO 8 or SEQ ID NO 9 or SEQ ID NO 14 or SEQ ID NO 15 of at least 75% or is the complementary sequence thereof. SEQ ID NO 8 is the cDNA sequence of CDC7 of *Arabidopsis thaliana*, comprising the coding sequence for the newly identified amino acid sequences (SEQ ID NOS 2, 3 and 4) as are discussed above. SEQ ID NO 9, is the cDNA sequence of CDC27 of *Arabidopsis thaliana*, includes the sequences coding for the newly identified amino acid sequences (SEQ ID NOS 6 and 7 and 12) as discussed above. SEQ ID NO 14 is the cDNA sequence of CDC27A2 of *Arabidopsis thaliana* and includes the sequences coding for the newly identified amino acid sequences (SEQ ID Nos 6 and 7) as discussed above but lacks the sequence coding for the newly identified amino acid sequence (SEQ ID NO 12).

SEQ ID NO 15 is the cDNA sequence of CDC27B of *Arabidopsis thaliana* and includes the sequences coding for the newly identified amino acid sequence (SEQ ID NO 10) as discussed above.

The presence of the amino acid sequences according to the present invention in DNA replication modulating proteins, in particular in CDC7 and CDC27 respectively, may play an important role in the biological function of the said proteins. Also, the sequences according to SEQ ID NOS 8 and 9 and 14 and 15, or parts thereof, can advantageously be used to isolate and identify homologntary sequence thereof. Such a DNA sequence codes for an amino acid sequence that till now was not known to be part of DNA replication modulating proteins, in particular of CDC7 and CDC27. It was now found, that DNA sequences, corresponding to the nucleotides 1229-1291, 2126-2187 and 2298-2385 of SEQ ID NO 8 code for new amino acid sequences of plant CDC7. The DNA sequence, corresponding to nucleotides 109-181 and 2125-2148 of SEQ ID NO 9 code for novel amino acid sequences of plant CDC27A1, of *Arabidopsis thaliana*. The DNA sequence, corresponding to nucleotides 109-181 and 2092-2148 of SEQ ID NO 14 code for novel amino acid sequences of plant CDC27A2 of *Arabidopsis thaliana*. The DNA sequence, corresponding to nucleotides 1-483 of SEQ ID NO 15 codes for novel amino acid sequence of plant CDC27B of *Arabidopsis thaliana*. Said DNA sequences may therefore in particular be used to identify and isolate genes or gene fragments from other plants or organisms that are homologous to the CDC7 or CDC27 sequence discussed above.

Probes and Primers

In a further embodiment, the DNA sequences according to the invention may be used as primers for use in a nucleic acid amplification technique. Said primers can be used in a particular amplification technique to identify and isolate substantially homologous nucleic acid molecules from other plant species. The design and use of said primers is known by the person skilled in the art. Preferably such amplification primers comprise a contiguous sequence of at least 6 nucleotides, in particular 13 nucleotides, preferably 15 to 25 nucleotides or more, identical or complementary to the nucleotide sequence encoding the amino acid sequence of SEQ ID Nos 1-7 and 10-13. Another application is the use as a hybridization probe to identify nucleic acid molecules hybridizing with a nucleic acid molecule of the invention by homology screening of genomic DNA or cDNA libraries. Furthermore, the person skilled in the art is well aware that it is also possible to label such a nucleic acid probe with an appropriate marker for specific applications, such as for the detection of the presence of a nucleic acid molecule of the invention in a sample derived from an organism, in particular plants. A number of companies such as Pharmacia Biotech (Piscataway N.J.), Promega (Madison WI.), and US Biochemical Corp (Cleveland OH) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like.

The nucleic acid sequence for a protein of the invention can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price (Blood Rev. 7 (1993), 127-134) and Trask (Trends Genet. 7 (1991), 149-154).

Vectors

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as *E. coli*, yeast, mammalian cell lines and other eukaryotic cell lines, for example insect Sf9 cells.

Preferably, a polynucleotide of the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators.

Vectors of the invention may be transformed or transfected into a suitable host cell as described below to provide for expression of a protein of the invention. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used, for example, to transfect or transform a host cell.

Control sequences operably linked to sequences encoding the protein of the invention include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers.

The promoter is typically selected from promoters which are functional in mammalian, cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of a-actin, b-actin, tubulin) or, alternatively, a tissue-specific manner (such as promoters of the genes for pyruvate kinase). Tissue-specific promoters specific for selected plant tissue cells are particularly preferred, see below in section "transgenic plants".

It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

Therefore, the invention relates to DNA vectors, particularly plasmids, cosmids, viruses, bacteriophages and other vectors used conventionally in genetic engineering that comprise a DNA sequence according to the invention. Methods which are well known to those skilled in the art can be used to construct various plasmids and vectors: see for example, the techniques described in Sambrook, Molecular Cloning A Laboratory Manual, Cold Spring Habor Laboratory (1989) N.Y. and Ausubel, Current Protocols in Molecular Biology, Green Publishing Associates and Wiley Interscience, N.Y. (1989), (1994). Said vector further preferably comprises a promoter, functional in plant cells, operably linked to the DNA sequence, according to the invention. With such a vector, the DNA sequence according to the invention can be expressed in plant cells and may modulate the DNA replication in the said cells.

Identifying Derivatives, Variants and Homologs of the Cell Cycle Interacting Proteins of the Invention In another embodiment, the present invention relates to a method for identifying and/or obtaining proteins capable of modulating the DNA repliction in plants, comprising a two-hybrid screening assay, using CDC27 or CDC7 polynucleotide sequences as a bait and a cDNA library of a cell suspension culture as prey.

The yeast two-hybrid assay is a genetic strategy developed to identify proteins (encoded by the cDNAs, the 'prey') able to interact in vivo with a known protein (the 'bait'). Interactions between proteins are detected through the reconstitution of the activity of a transcription activator and the subsequent expression of a reporter gene. The cell culture may be from any organism possessing cell cycle interacting proteins such as animals, preferably mammals. Particularly preferred are plant cell suspension cultures such as from *Arabidopsis*. The nucleic acid molecules encoding proteins or peptides identified to interact with CDC7 or CDC27 in the above mentioned assay can be easily obtained and sequenced by methods known in the art. Therefore, the present invention also relates to a DNA sequence encoding a cell cycle interacting protein obtainable by the method of the invention.

Transgenic Plants

To analyse the industrial applicabilities of the invention, transformed plants can be made using the nucleotide sequences according to the invention. Such a transformation of the new gene(s), proteins or inactivated variants/muteins thereof will either positively or negatively have an effect on cell division. Methods to modify the expression levels and/or the activity are known to persons skilled in the art and include for instance overexpression, co-suppression, the use of ribozymes, sense and anti-sense strategies, gene silencing approaches. "Sense strand" refers to the strand of a double-stranded DNA molecule that is homologous to a mRNA transcript thereof. The "anti-sense strand" contains an inverted sequence which is complementary to that of the "sense strand".

Hence, the nucleic acid molecules according to the invention are in particular useful for the genetic manipulation of plant cells in order to modify the characteristics of plants and to obtain plants with modified, preferably with improved or useful phenotypes. Similarly, the invention can also be used to modulate the cell division and the growth of cells, preferentially plant cells, in vitro cultures. A transformed plant can thus be obtained by transforming a plant cell with a gene encoding a polypeptide concerned or fragment thereof alone or in combination. For this purpose tissue specific promoters, in one construct or being present as a separate construct in addition to the sequence concerned, can be used.

Thus, the present invention relates to a method for the production of transgenic plants, plant cells or plant tissue comprising the introduction of a nucleic acid molecule or vector of the invention into the genome of said plant, plant cell or plant tissue.

The invention further relates to a method for modulating DNA replication in plant cells, plant parts or plants by conferring to one or more plant cells the capacity to provide a protein, or a mutein thereof according to the invention, in an amount sufficient to modulate DNA replication and/or to block mitosis of the said cells.

In particular, the said capacity is conferred to one or more plant cells, by a) transforming one or more plant cells with DNA according to the invention or with a vector according to the invention, b) maintain or culture the plant cells in order to regenerate plant parts or plants from the transformed cells c) incubating the cells, plant parts or plants at conditions, allowing expression of the DNA according to claim 11 or 12, to produce a protein according to the invention or a mutein thereof according to the invention. For the expression of the nucleic acid molecules according to the invention in sense or antisense orientation in plant cells, the molecules are placed under the control of regulatory elements which ensure the expression in plant cells. These regulatory elements may be heterologous or homologous with respect to the nucleic acid molecule to be expressed as well with respect to the plant species to be transformed. In general, such regulatory elements comprise a promoter active in plant cells. To obtain expression in all tissues of a transgenic plant, preferably constitutive promoters are used, such as the 35 S promoter of CaMV (Odell, Nature 313 (1985), 810-812) or promoters of the polyubiquitin genes of maize (Christensen, Plant Mol. Biol. 18 (1982), 675-689). In order to achieve expression in specific tissues of a transgenic plant it is possible to use tissue specific promoters (see, e.g., Stockhaus, EMBO J. 8 (1989), 2245-2251). Known are also promoters which are specifically active in tubers of potatoes or in seeds of different plants species, such as maize, Vicia, wheat, barley etc. Inducible promoters may be used in order to be able to exactly control expression. An example for inducible promoters are the promoters of genes encoding heat shock proteins. Also microspore-specific regulatory elements and their uses have been described (WO96/16182). Furthermore, the chemically inducible Tet-system may be employed (Gatz, Mol. Gen. Genet. 227 (1991); 229-237). Further suitable promoters are known to the person skilled in the art and are described, e.g., in Ward (Plant Mol. Biol. 22 (1993), 361-366). The regulatory elements may further comprise transcriptional and/or translational enhancers functional in plants cells. Furthermore, the regulatory elements may include transcription termination signals, such as a poly-A signal, which lead to the addition of a poly A tail to the transcript which may improve its stability.

Methods for the introduction of foreign DNA into plants are also well known in the art. These include, for example, the transformation of plant cells or tissues with T-DNA using *Agrobacterium tumefaciens* or *Agrobacterium rhizogenes*, the fusion of protoplasts, direct gene transfer (see, e.g., EP-A 164 575), injection, electroporation, biolistic methods like particle bombardment, pollen-mediated transformation, plant RNA virus-mediated transformation, liposome-mediated transformation, transformation using wounded or enzyme-degraded immature embryos, or wounded or enzyme-degraded embryogenic callus and other methods known in the art.

In general, the plants which can be modified according to the invention and which either show overexpression of a protein according to the invention or a reduction of the synthesis of such a protein can be derived from any desired plant species. They can be monocotyledonous plants or dicotyledonous plants, preferably they belong to plant species of interest in agriculture, wood culture or horticulture interest, such as crop plants (e.g. maize, rice, barley, wheat, rye, oats etc.), potatoes, oil producing plants (e.g. oilseed rape, sunflower, pea nut, soy bean, etc.), cotton, sugar beet, sugar cane, leguminous plants (e.g. beans, peas etc.), wood producing plants, preferably trees, etc. The invention further relates to progeny of such plants and to plant material such as roots, flowers, fruit, leaves, pollen, seeds, seedlings or tubers, obtainable from the plant according to the invention.

The invention further relates to a plant cell, transformed with a vector according to the present invention, or comprising DNA according to the present invention. The invention also relates to plants, obtainable by the method according to the present invention and to progeny of such a plant and to plant material, such as roots, flowers, fruit, leaves, pollen, seeds, seedlings or tubers, obtainable from the plant according to the invention.

Mutants

In further embodiments of the invention, expression of dominant negative mutants of CDC7 or CDC27 are used to modulate DNA replication in plant cells, plant tissues, plant organs and/or whole plants. These embodiments involve the overexpression of a mutein or mutant gene according to the present invention which will inhibit the function of a wild-type allele when expressed in the same cell, thereby the phenotype of a transgenic plant, plant organ or plant cell expressing the mutant will be that of a blocked cell cycle progression.

Herskowitz, Nature 329: 219-222 (1987), reviews the inactivation of genes by interference at the protein level, which is achieved through the expression of specific genetic elements encoding a polypeptide comprising both intact, functional domains of the wild type protein as well as nonfunctional domains of the same wild type protein. Such peptides are known as dominant negative mutant proteins.

Examples of dominant negative mutants are given below.

CDC7 Dominant Negative Mutant—Nematode Resistance

In a special embodiment of the present invention, a DNA vector comprises DNA, coding for a mutein according to the present invention, that is operably linked to a nematode-induced promoter, said promoter functional in plant cells. Nematode infection of plants may cause severe problems to plant growth and crop generation. After penetrating the roots of their hosts, nematodes induce, at the infection sites, the development of feeding cells, specialised in the uptake of solutes from the vascular system of the plant. These infection sites are of crucial importance for the development for the parasite. In this way, root-knot nematodes induce multinucleated giant cells in the infected plant with highly elevated DNA contents. By specifically blocking the DNA synthesis in the feeding cells, the formation of the said multinucleated giant cells may be blocked, so that the nematodes may not further develop. One can contemplate that a CDC7 mutein, which is not further capable to induce the onset of the DNA synthesis, e.g. by loss of one or more phosphorylation sites or loss of binding function to a plant homolog of yeast DBF4 (Jackson et al 1993 Mol Cell Biol 13, 2899-2908) could, when present in sufficient amounts, block the onset of the DNA synthesis. When DNA, coding for such a mutein, and under the control of a promoter, functional in plant cells and inducible by the presence of nematodes in or in the vicinity of the plant cells, is comprised in the plant cells, the mutein can be expressed in the presence or vicinity of nematodes. This may lead to a DNA synthesis block, therewith avoiding further nematode development. The advantage of such a system is the fact that the plant is not producing any heterologous nematocide, that may be harmful for the plant itself. Such a system is not restricted to CDC7. The person, skilled in the art, aware of this application, will be well aware of the possibilities to take other DNA replication modulating proteins, such as CDC27 for developing an analogous anti-nematode system.

CDC27 Mutant—Endoreduplication

A further embodiment of the invention involves the down regulation of CDC27. A further embodiment of the invention involves the downregulation of CDC27 resulting in suppression of the APC complex, modulation of DNA replication and/or blocking mitosis. This can be achieved by expression of CDC27 point mutants. An alternative strategy can be envisaged involving a CDC27 mutein consisting of a block of TPR tandem repeats. Such a mutein is still likely to interact with other TPR-containing proteins from the APC such as CDC16 and CDC23 or APC regulator proteins such as PP5. As such, APC component proteins or APC regulator proteins would probably be titrated out and normal APC function be prevented. Based on results already obtained from experiments designed to delineate TPR domains involved in the interaction between two TPR proteins (Lamb et al. 1984, EMBO J 13, 4321-4328; Ollendorf and Donoghue 1997, J Biol Chem 272, 32011-32018), this strategy might indeed would prove valuable. Overexpression of CDC27 muteins, via the effect on the APC, can be used to enhance endoreduplication in plant cells, plant tissues, plant organs, or whole plants.

For example, as is described above, a CDC27 mutein wherein the SEQ ID No 7 has been mutated, leading to the incapability of this mutein to bind with other factors of the APC can be mentioned. The mutated protein would be still able to interact with the substrate, therewith titrating out the APC, abolishing or at least seriously reducing the APC-function, leading to the formation of polyploid cells. Also, mutations in SEQ ID No 6 or 10 could render the mutein incapable of interacting with the substrate but still capable of binding with the other factors of the APC-complex. The result is the generation of a dominant negative, as the complex will not be able to drive the destruction of key components of the cell cycle machinery, responsible to control the number of DNA-replication cycles.

By manipulating the level of endoreduplication one can increase the storage capacity of, for example, endosperm cells. Thus, another aspect of the current invention is that one or more DNA sequences, vectors or proteins, regulatory sequences or recombinant DNA molecules of the invention can be used to modulate, for instance, endoreduplication in storage cells, storage tissues and/or storage organs of plants or parts thereof.

Preferred target storage organs and parts thereof for the modulation of endoreduplication are, for instance, seeds (such as from cereals, als, oilseed crops), roots (such as in sugar beet), tubers (such as in potato) and fruits (such as in vegetables and fruit species). Furthermore it is expected that increased endoreduplication in storage organs and parts thereof correlates with enhanced storage capacity and as such with improved yield. In yet another embodiment of the invention, a plant with modulated endoreduplication in the whole plant or parts thereof can be obtained from a single plant cell by transforming the cell, in a manner known to the skilled person, with the above-described means.

CDC27 and CDC7 Mutants—Sterile Plants

Another embodiment of the invention relates to a method for modulating DNA replication and the resultant generation of male or female sterile plants. This would be achieved by the expression of dominant negative mutants of either cdc7 or cdc27 under the control of very specific promoters—either from male or female gametophytes—to block cell division and disrupt meiosis. The resulting plants would be naturally sterile.

Overexpression of CDC7 and DBF4 Activate DNA Synthesis

Another embodiment of the invention relates to a method for the generation of plant cells, plant tissues, plant organs, or whole plants with the capacity for the overexpression of CDC7 in combination with a plant homolog of Dbf4 thereby modulating DNA replication. Results in yeast indicate that the association of Dbf4 with CDC7 is essential for the G1 to S transition, namely DNA synthesis (Ohtoshi A, Miyake T, Arai K, Masai H; Mol Gen Genet 254(5): 562-70 May 20, 1997). Therefore in the present invention, by overexpressing both CDC7 and Dbf4 proteins, one can activate, stimulate or initiate DNA synthesis in cells where DNA synthesis does not normally take place, such as cells that have already gone through the cell cycle. As a consequence the amount of DNA is increased in the cell therewith manipulating the level of endoreduplication as is outlined above.

Polyploid Plants

Another embodiment of the invention relates to the generation of polyploid plant cells, plant parts or plants.

If for example, plant cells are transformed with a vector, comprising the coding sequence of plant CDC27, according to the present invention, under the control of a suitable promotor and optionally other expression controlling elements, these plant cells may produce CDC27. When the said plant cells produce CDC27 protein in a sufficient amount, extra rounds of DNA replication may take place before mitosis, leading to polyploid cells.

BRIEF DESCRIPTION OF THE DRAWINGS

Characterisation of CDC7 and CD27 Genes

The architecture of the CDC7 and CDC27 genes are illustrated in FIGS. 1 and 2 and 5.

The total length of the coding sequence is 2667 nucleotides, coding for 889 amino acids. The fifth, eleventh and thirteenth exons comprise novel coding sequence; in FIG. 1, the corresponding boxes are black. It is to be understood, and obvious to a skilled person, that the first and the last triplet of the coding sequence of an exon, may partially be encoded by the last two or one nucleotide(s) from the adjacent downstream exon, and, accordingly, by the first two or one nucleotide(s) of the adjacent upstream exon.

Figure 5:
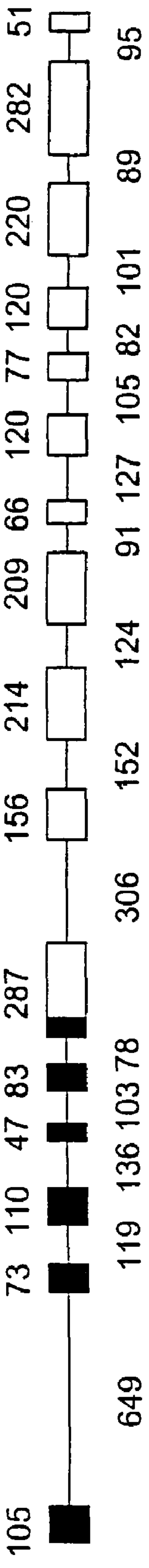

The first 5 exons (black in FIG. 5) and part of the $6^{th}$ exon (black in FIG. 5) comprise novel coding sequences and were not identified in the known genomic CDC27B sequence of *Arabidopsis thaliana* (see text). The entire sequence comprises 2151 nucleotides, corresponding to 716 amino acids.

Figure 1:
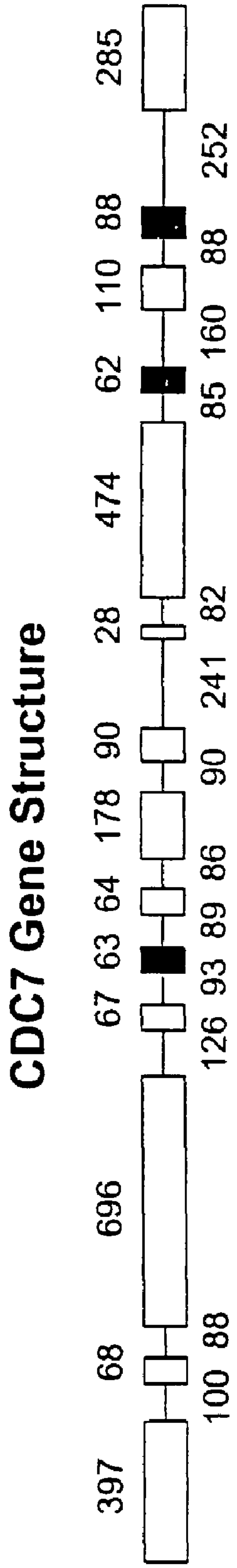
FIG. 1 illustrates the genomic architecture of the *Arabidopsis* CDC7 gene, wherein the exons are boxed. The numbers above the box indicate the length of the exon, the number below and between two boxes indicates the length of the intron.
Figure 2:
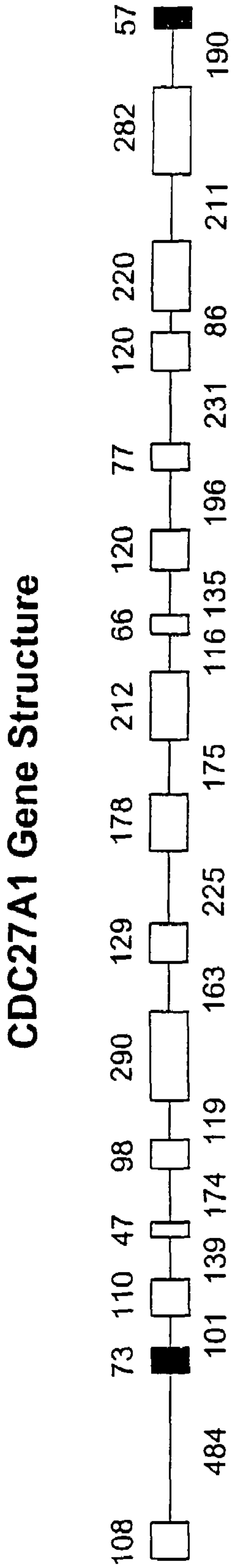
In FIG. 2 and 5, the genomic architecture of the CDC27A1 and CDC27B genes, respectively, of *Arabidopsis thaliana* are depicted as explained for FIG. 1. The second and the sixteenth (last) exon (black in FIG. 2) comprise novel coding sequences and were not identified in the known genomic CDC27A1 sequence of *Arabidopsis thaliana* (see text). The entire sequence comprises 2184 nucleotides, corresponding to 727 amino acids.
Figure 3:
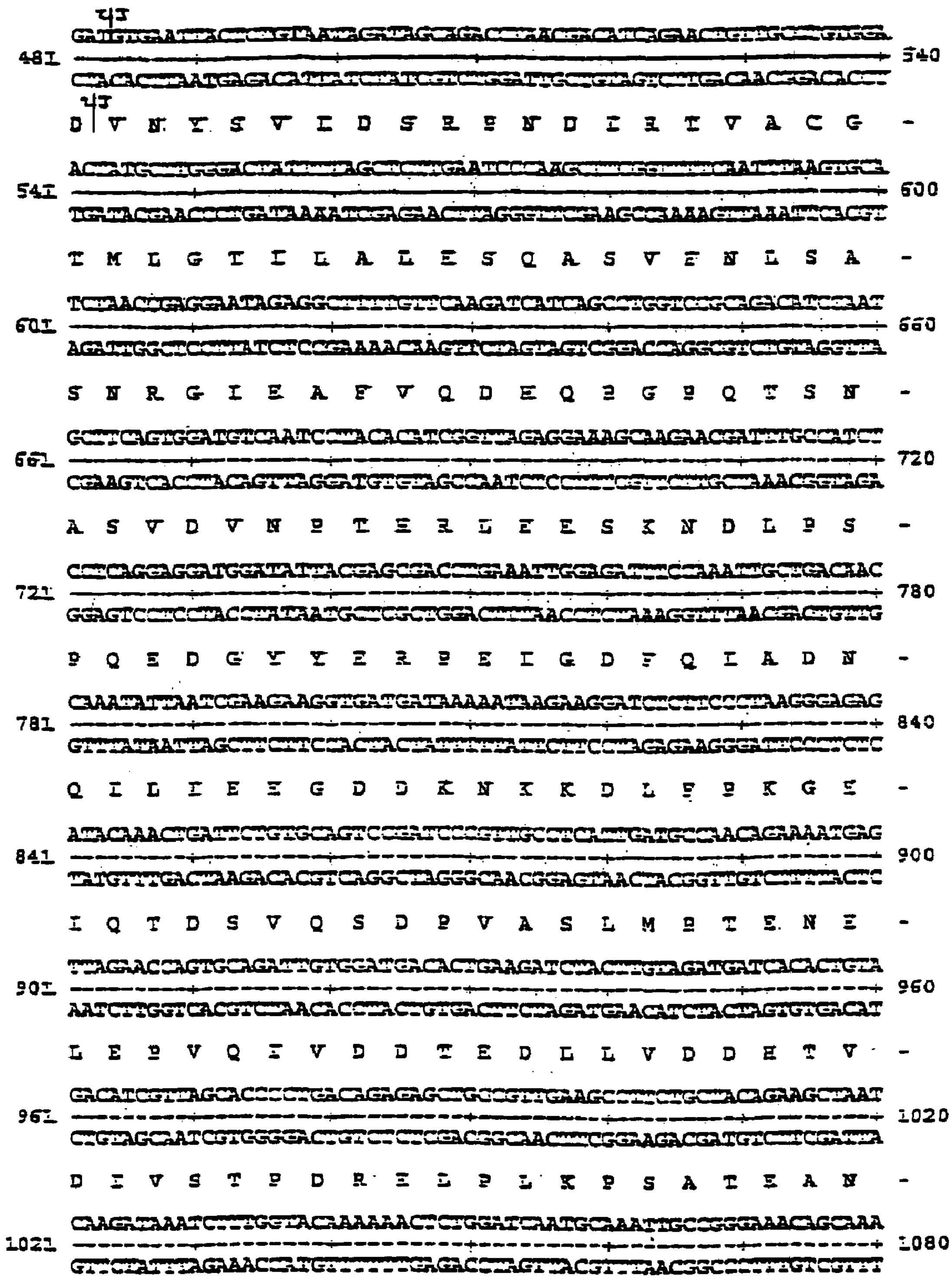

In FIGS. 3 and 4, the complete cDNA sequence of CDC7 (SEQ ID NO: 1) and CDC27A1 (SEQ ID NO: 5), respectively, according to the present invention are depicted, with the respective encoded amino acid sequence therebelow (SEQ ID NO: 8 and 9, respectively). Vertical lines in the nucleotide sequence indicate the exon boundaries, i.e. $^{2}|^{3}$ is the boundary between exons 2 and 3. The exon boundaries are derived from genomic CDC7 and CDC27A1 sequences (see examples 1 and 2 respectively). Such lines are also drawn in the amino acid sequence, although, as is indicated above, the amino acids, flanking such a vertical line, may be partially encoded by the adjacent exon. Exact positioning of the vertical line is in such a case not possible and is set at the left or the right of such an amino acid in an arbitrary manner. See examples 1 and 2 for further details.

An alignment of the CDC27A1 (SEQ ID NO 5) and CDC27B (SEQ ID NO 13) amino acid sequences is given in FIG. 6 with indication of SEQ ID NOS 6, 7, 10 and 12. Said CDC27A1 and CDC27B sequences are 49% identical when gaps are introduced in the sequences to ensure optimal alignment and maximal identity.

Figure 7:
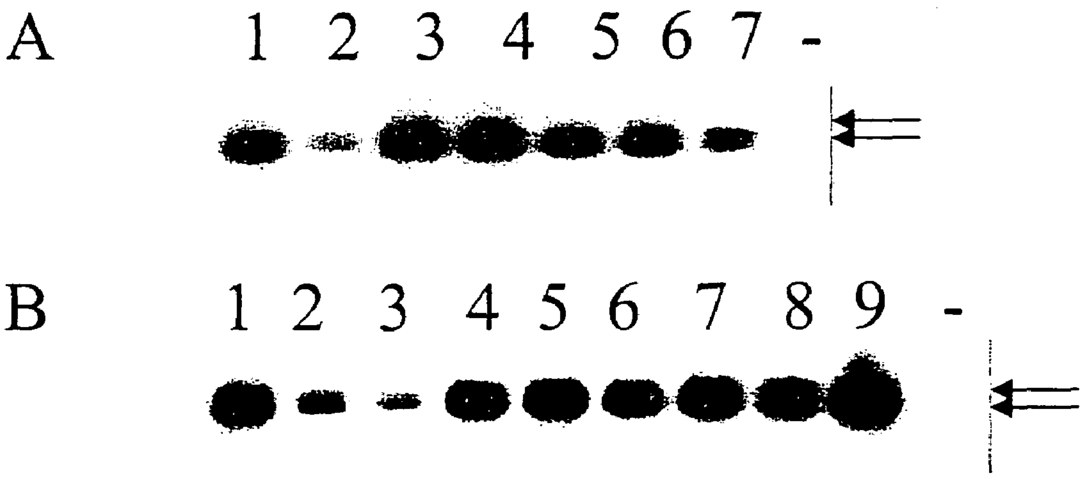
Figure 8:
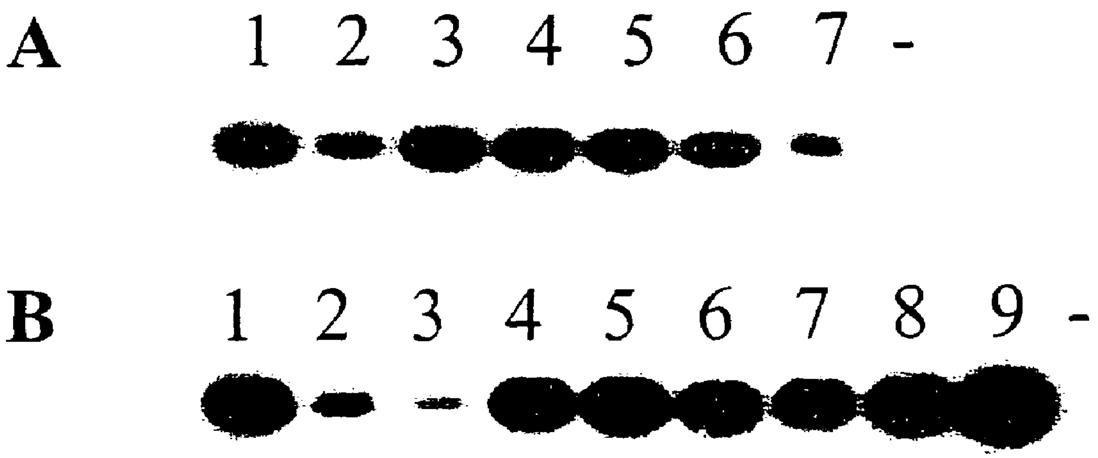

In FIGS. 7 and 8, the expression of CDC27A and CDC27B genes is illustrated. FIG. 7A shows expression of CDC27A genes (both CDC27A1 and CDC27A2 are detected; indicated by the arrows) in several *Arabidopsis thaliana* tissues: 1-etiolated seedlings; 2-flowers; 3-buds; 4-stems; 5-leaves; 6-roots; siliques; –negative control. FIG. 7B shows the expression of CDC27A genes in *Arabidopsis thaliana* root cultures treated with different substances: 1-abscisic acid (ABA); 2-2,4-dichlorophenoxyacetic acid (2,4-D); 3-hydroxyurea; 4-kinetin; 5-kinetin+1-naphthaleneacetic acid (NAA); 6-NAA; 7-oryzalin; 8-starvation; 9-untreated control roots; –negative control. FIG. 8A shows the expression of the CDC27B gene in several *Arabidopsis thaliana* tissues as outlined in FIG. 7A. FIG. 8B illustrates the expression of the CDC27B gene in *Arabidopsis* root cultures treated with different substances as outlined in FIG. 7B.

The invention will now be further illustrated by the following examples, that are not intended to limit the scope of the invention.

EXAMPLES

Although in general the techniques mentioned herein are well known in the art, reference may be made in particular to Sambrook et al., Molecular Cloning, A Laboratory Manual (1989) and Ausubel et al., Current Protocols in Molecular Biology (1995), John Wiley & Sons, Inc. Further, scientific explanations and reasonings in the examples are given for illustrative reasons only, without however being bound thereto.

Example 1

Isolation of an *Arabidopsis* CDC7 Homologue

Conserved regions of the *Saccharomyces cerevisae* and *Schizosaccharomyces pombe* CDC7 homologue genes were used to synthesize degenerated oligonucleotides to amplify an *Arabidopsis* CDC7 homologue cDNA fragment. These oligonucleotides were as follows:

```
1 (sense)
5' AAA/G ATA/C/T GGA/C/G/T GAA/G GGA/C/G/T
ACA/C/G/T TT 3'

2 (sense)
5' ATA/C/T ATA/C/T CAC/T AGA/G GAA/G ATA/C/T AA 3'

3 (antisense)
5' AG C/TTC A/C/G/TGG A/C/G/TGC C/TCT A/GAA
A/C/G/TCC 3'

4 (antisense)
5' AC A/C/G/TCC A/C/G/TA/GC A/GCT CCA A/C/G/TAT
A/GTC 3'
```

First strand cDNA prepared from whole *Arabidopsis* plants using the Superscript Preamplification System from Life Technologies was used as template in nested PCR reactions. The first reaction was carried using the pair of oligos 1 and 4, and the second reaction used oligos 2 and 3. PCR conditions were essentially as described (Ferreira et al. 1991). A fragment of approximately 650 bp was eluted from an agarose gel, cloned in pGEM-T and sequenced. Sequencing comparison using the GCG-package version 9.1 showed that the deduced amino acid sequence of the PCR fragment has approximately 40% homology to the published yeast CDC7 sequences. This fragment was then used to screen a lambda gt10 cDNA library prepared from total *Arabidopsis* plants. The largest cDNA isolated, approximately 1,2 kb, was completely sequenced by the dideoxy method. This *Arabidopsis* cDNA contains an open reading frame encoded encoding a polypeptide of 384 amino acids (amino acid 473 to amino acid 856 in FIG. 3). With the SRS search program the EMBL and EMBLnew databanks were screened for gene sequences designated or annotated with the term cdc7. One genomic sequence from *Arabidopsis thaliana* was found (accession number Z97342). This submitted genomic sequence comprised a predicted gene, indicated as "having similarity to protein kinase HSK of fission yeast", having 11 exons and coding for a protein having 829 amino acids.

With the GCG-package version 9.1, the said genomic sequence was compared with the identified partial cDNA sequence, using the "best-fit program". The identified cDNA-sequence covered nucleotides 119827 to 121978 of the genomic sequence of Z97342.

The identified cDNA-sequence did not correspond with the complete coding sequence of the predicted gene on the Z97342 sequence. Within the present cDNA sequence, two additional coding sequences (additional exons) were identified, namely nucleotides no 120770-120709 and 120350-120263 of Z97342, coding for the amino acid sequences of SEQ ID NOS 3 and 4 respectively.

Upon comparison with the genomic *Arabidopsis* sequence, it however appeared that the present cDNA was not complete. To complete our cDNA at the 5' side we used the CAP-finder kit (Clontech), using the primers (CTCTCCCATCTGGTCATGTC, #1; GAACATGCAGTAGCCGTACC, #2) specified for the cDNA, in nested PCR reactions. For the missing 3' end, two nested sequences specific for the cDNA (AAATGGTGCGAACTCAACAC, #2) and (TATGGGAAGTAGCCAAGCTG, #1) and an anchored oligo-dT on the lower strand were used. PCR conditions were essentially as described (Ferreira et al., 1991). The fragments were eluted from agarose gel and cloned using standard techniques and sequenced. The deduced amino acid sequence encoded by the PCR fragment showed clear homology to the yeast published CDC7 sequences and matched with an the above mentioned *Arabidopsis* genomic sequence. The DNA-fragment, comprising the missing 5' terminal sequence, comprised an additional coding sequence of 63 nt (nrs 122340 to 122278 in Z97342) not identified in Z97342, coding for the amino acid sequence of SEQ ID NO 2.

With the obtained sequences, the complete cDNA for the CDC7 homologue of *Arabidopsis thaliana* could be reconstructed, which is illustrated in FIG. 3 and in SEQ ID NO 8.

The presently identified CDC7 cDNA comprises additional novel coding sequences, corresponding to novel exons (nos 5, 11 and 13 in FIG. 3), that were not identified in Z97342, and codes for a protein of 890 amino acids.

Example 2

Isolation of the *Arabidopsis* CDC27A1 Gene and cDNA

Conserved regions of the published CDC27 homologue genes (Sikorski et al., 1991 Cold Spring Harbor Symposia on Quantitative Biology vol LVI, 663-673, 1991) were used to synthesize degenerated oligonucleotides to amplify *Arabidopsis* CDC27 cDNA. The oligonucleotides were as follows:

```
1 (sense)
5' TGG GTA/C/G/T TTA/G GCA/C/G/T A/CAA/G GG 3'

2 (sense)
5' ATG GAA/C/G/T G/ATT/C/A TA/TC/T AGA/C/G/T AC 3'
```

-continued

```
3 (antisense)
5' AGA/G CAT/C TAT/C AAT/C GCA/C/G/T TGG 3'

4 (antisense)
5' TA T/A/G AC/T CAT A/C/G/TCC C/TAA A/C/G/CC
A/GAA 3'
```

First strand cDNA prepared from flower buds was used as template in nested PCR reactions. The first reaction was carried using the pair of oligos 1 and 4, and the second reaction used oligos 2 and 3. PCR conditions were as described (Ferreira et al., 1991, Plant Cell 3, 531-540), except that the annealing temperature of the first reaction was 45 C, and for the second reaction, 37 C was used. A fragment of approximately 300 bp was eluted from agarose gel and cloned in pGEM-T. Out of 16 clones sequenced, two showed high homology to published CDC27 sequences (Sikorski et al., 1991 Cold Spring Harbor Symposia on Quantitative Biology vol LVI, 663-673, 1991). This fragment was then used to screen a lambda gt10 cDNA library prepared from total *Arabidopsis* plants. The isolated target cDNA, approximately 2,5 kb, was completely sequenced by the dideoxy method and is shown in FIG. 4 and in SEQ ID nr 9. A combination of restriction enzymes and oligonucleotide subcloning was used to produce the templates for sequencing.

The *Arabidopsis* CDC27A1 cDNA contains one open reading frame, encoding a polypeptide of 727 amino acids (FIG. 4). With the SRS search program, the databanks EMBL and EMBL new were screened for gene sequences, homologous to the present CDC27 cDNA sequence. A genomic sequence from *Arabidopsis thaliana* (accession number AC001645) was found, comprising 14 exons, coding for a protein of 727 AA. With the GCG-package version 9.1, the present cDNA-sequence was compared with the said genomic *Arabidopsis* sequence (1) using the "best fit"-program. It appeared that the present cDNA comprised additional coding information for two novel exons, namely the second and last exon of the *Arabidopsis* CDC27-gene (exons 2 and 16 in FIG. 4).

The amino acid sequences encoded by the second and last exon are depicted in SEQ ID NOS 6 and 7 respectively.

Example 3

Dominant Negative Mutants of CDC7

Dominant negative mutants of CDC7 (CDC7 DN) are constructed by creating substitution mutations including amino acid residues 1(G), 5(V), 18(A) and 20(K) of SEQ ID No2; amino acid residues 13(T), 16(F), 18(A) and 20(E) of SEQ ID No3; amino acid residues 7(L) and 18(K) of SEQ ID No4. Substitutions are not conservative. Expression of a CDC7 DN in a whole plant, a plant tissue, a plant organ or a plant cell results in cell cycle arrest at G1/S. These results are in line with the situation in yeast, wherein one such substitution, threonine 13 of SEQ ID No 3 (position 722 in SEQ ID No 1) to a glutamate has proven to create a dominant negative CDC7 in yeast. This CDC7 DN is inactive as a kinase but can still bind DBF4, thus preventing activation of wild-type CDC7 molecules (Ohtoshi et al. 1997, Mol Gen Genet 254, 562-570).

The CDC7 DN mutants can be obtained by site-directed mutagenesis using the ExSite PCR-based site-directed mutagenesis kit (Stratagene, La Jolla, CA.). Fidelity of the mutagenesis are confirmed by sequencing.

Example 4

Mutants of CDC27

Several types of CDC27 muteins can be considered:

(1) Insertion of an amino acid such as proline (P) in the amino acid sequence SEQ ID No 7, e.g. behind the tyrosine (Y) residue leads to a loss-of-function of the APC. It is believed that such an insertion deforms the predicted ($\alpha$ helix of the novel TPR-like domain of which SEQ ID No 7 is part and causes a disturbance of the overall three-dimensional structure of CDC27, therewith titrating out functional proteins of the APC, such as CDC16 or CDC23, leading to loss of APC function. In line with these results, altering the $\alpha$ helix structure in one of the TPR units of yeast CDC27 has been proven, and of any of the TPR units has been hypothesized, to destroy CDC27 function (Lamb et al. 1984, EMBO J. 13, 4321-4328).

(2) Deletion of the NH2-terminal 100 to 220 or 200 to 220 amino acids of CDC27 also leads to loss of function of the APC by titrating out molecules such as APC substrates or APC regulators. This domain encompasses the conserved amino acid sequence SEQ ID No 6 as well as the first TPR unit of CDC27. Deletion of this sequence in human CDC27 abrogates binding of e.g. CDC16, but not of that of e.g. PP5, an APC regulator protein (Ollendorf and Donoghue 1997, J Biol Chem 272, 32011-32018).

(3) CDC27 muteins consisting of the conserved NH2-terminal domain (containing SEQ ID No6) and 1, 2 or more of the downstream TPR units.

(4) CDC27 muteins consisting of the novel TPR-like domain (ending with SEQ ID No7) preceded by 1, 2 or more of the upstream TPR units.

Muteins described in (3) and (4) act as those described in (1) or (2).

The point mutants in (1) are obtained by site-directed mutagenesis using the ExSite PCR-based site-directed mutagenesis kit (Stratagene, La Jolla, CA.). Fidelity of the mutagenesis are confirmed by sequencing. Deletion mutants in (2), (3) and (4) are obtained by high-fidelity PCR (Expand High Fidelity PCR System, Boehringer, Mannheim) using primers designed to amplify the desired stretches of the CDC27 nucleotide sequence. Primers include extensions recognized by restriction endonucleases to allow easy cloning in a vector such as pUC18. Amplified sequences are checked by nucleotide sequence determination.

Expressing such CDC27 muteins in a whole plant, a plant tissue, a plant organ or a plant cell will cause malfunctioning of the APC and thus repetitive cycles of DNA synthesis without intervening mitosis. This endoreduplication results in a polyploid phenotype.

Example 5

Nematode Resistance CDC7 DN

In order to obtain nematode resistance, the CDC7 DN coding sequence is operably linked to a plant promoter responsive to nematode infection and to the NOS polyadenylation site. The ARM1 or Att0728 promoters can be used (Barthels et al. 1997, Plant Cell 9, 2119-2134). The CDC7 DN expression cassette is subsequently transferred to a binary vector such as pGSC1704 and the resulting vector electroporated into *Agrobacterium tumefaciens* C58C1RifR (pGV2260). Transformants are selected on streptomycin/spectinomycin containing medium and checked for the presence of the integral transformed binary vector. *Arabidopsis*

*thaliana* Col-0 is transformed with the selected *A. tumefaciens* strain by the floral dip method (Clough and Bent 1998, Plant J 16, 735-743). Transgenic plants are selected after seed germination in the presence of hygromycin. Selected transgenic lines and untransformed control lines are infected with root knot or cyst nematodes. Successfulness of infection is scored visually two weeks after inoculation (in vitro infection) or six weeks after inoculation (infection of soil-grown plants). Transgenic lines are considered resistant relative to control plants when they display a significant decrease in the number of females or cysts on roots and/or a significantly reduction in nematode feeding sites and/or egg production and/or viable nematodes in the eggs.

Example 6

Male Sterility CDC7 DN and CDC27 Muteins

Male sterility in plants are obtained by disrupting normal pollen development. This is achieved by preventing normal cell division of tapetum cells in the anthers. Operably linking CDC7 DN or CDC27 mutein to a tapetum-specific promoter such as Osg6B (Tsuchiya et al. 1995, Plant Cell Physiol 36, 487-494) and to a NOS polyadenylation site will result in a suitable expression cassette. Introduction of this cassette into *A. thaliana* is done as described in example 5. Selected transformant lines have a reduced and/or abnormal pollen formation/development. This is assessed using microscopic methods.

Example 7

Endoreduplication CDC27 Muteins

Any of the muteins are operably linked to a constitutive promoter such as the CaMV 35S promoter (Kay et al. 1987, Science 236, 1299-1302) or to a seed endosperm-specific promoter such as from a 2S albumin seed storage protein (Guerche et al. 1990, Plant Cell 2, 469-478) or to the BLZ2 promoter (Carbonero et al, 1999 in press) and to a polyadenylation signal. Such expression cassettes are transferred to A. thaliana as described in example 5. Selected transformant lines have a general higher rate of endoreduplicating cells (CaMV 35S promoter) and/or produce seeds with a higher amount of polyploid endosperm cells (2S albumin promoter). Endoreduplication or polyploidism is assessed in several ways.

Confocal microscopy is applied to measure the nuclear diameter. Polyploid cells normally have enlarged nuclei in order to harbor the increased DNA content.

The DNA content of plant cells is measured by flow cytometry (Galbraith et al. 1991, Plant Physiol 96, 985-989).

The cyclin B-degrading activity of the APC is determined as described by King et al. (1995, Cell 91, 279-288).

Example 8

CDC27 Gene Expression Analysis by RT-PCR

First-strand cDNA was prepared from RNA isolated from different *Arabidopsis thaliana* tissues (etiolated seedlings, flowers, flower buds; stems; leaves; roots; siliques) and from *Arabidopsis thaliana* root cultures treated for 48 h with different chemical substances ($10^{-6}$ M abscisic acid; $10^{-7}$ M 2,4-dichlorophenoxyacetic acid; 100 mM hydroxyurea; $10^{-6}$ M kinetin; $10^{-6}$ M kinetin+$10^{-6}$ M 1-naphthaleneacetice acid; $10^{-6}$ M 1-naphthaleneacetic acid; 2% (w/v) oryzalin). PCR was performed with these cDNAs using CDC27A-specific primers (sense primer 5' CCG TAG TGC TAG AAT AGC A 3' and antisense primer 5' AGT CAG CGT TGA AGT c3') or CDC27B-specific primers (sense primer 5' TCT CTC GAG GAA GAA AGG CAA CAA 3' and antisense primer 5' GGT TCT TGG AGT AGC TAT GGT TTC 3'). The resulting fragments generated by PCR were seperated in an agarose gel, blotted to a nylon membrane and hybridized with an $^{32}P$ labeled CDC27A or CDC27B DNA probe. Results are shown in FIG. 7 for CDC27A where the arrows indicate the presence of 2 bands, differing by 30 nucleotides. Sequencing of both fragments showed that they are identical, except for the 30 bp insertion. FIG. 8 illustrates the results for CDC27B.

The pictures in FIGS. 7 and 8 are representative of 3 independent experiments. Both genes are expressed in all plant tissues, but at reduced levels in open flowers an siliques. Expression of both genes is not drastically affected by hormone treatments, except for a reduction in expression levels observed when roots were incubated with 2,4-D (2,4-dichlorophenoxyacetic acid).

Ubiquitin specific primers were used in separated RT-PCR reactions, using the same first strand cDNAs and, after hybrization, the ubiquitin signals were used to normalize the experiments with CDC27A and CDC27B (data not shown). While the results of the experiments with hydroxyurea and oryzalin that are shown suggest a reduction in CDC27A expression levels when roots are treated with hydroxyurea. If these experiments are normalized with the results of ubiquitin experiments the difference is not significant. However, a decrease in CDC27B expression is observed in hydroxyurea treated roots, even when the results are normalized with ubiquitin. This result would indicate that CDC27B expression could be cell cycle regulated.

Example 9

Isolation of an *Arabidopsis* CDC27A2 cDNA

The RT-PCR products obtained with the CDC27A-specific primers as defined in Example 8 were cloned. CDC27A clones corresponding to the transcripts of different sizes (see FIG. 7) were identified and their nucleotide sequences determined. This revealed that both type of CDC27A clones had identical nucleotide sequences with the exception of a stretch of 33 nucleotides which was absent from the shorter CDC27A cDNA. Hence, the longest CDC27A cDNA is referred to as CDC27A1 (SEQ ID NO 9) whereas the shorter CDC27A cDNA is referred to as CDC27A2 (SEQ ID NO 14).

Example 10

Isolation of an *Arabidopsis* CDC27B Gene and cDNA

By means of in silico cloning a second *Arabidopsis thaliana* CDC27 homologue was identified with GenBank accession number AC006081. The GeneMark software was used to predict the exon-intron structure of the gene (see FIG. 5) and it was observed that the animo acid sequence of the protein derived from the predicted open reading frame comprised an extra 161 amino acids at the $NH_2$-terminus as compared to the GenBank sequence. Subsequently the coding region was isolated by PCR on cDNA using primer lying immediately outside of the predicted open reading frame. A product of the expected size was obtained, cloned and its nucleotide sequence determined to confirm the predicted open reading frame. The primers used to clone the open reading frame were: sense primer 5' TCT CTC GAG GAA GAA AGG CAA CAA 3' and antisense primer 5' GGT TCT TGG AGT AGC TAT GGT TTC 3'. The new *Arabidopsis* CDC27 homologue is referred to as CDC27B.

The CDC27A1 and CDC27B proteins are aligned in FIG. 6 and are only 49% identical.

---

What is claimed is:

1. A method for the production of a transgenic plant, plant cell or plant tissue comprising introduction into the genome of the plant, plant cell or plant tissue of a nucleic acid encoding a CDC27B polypeptide or homolog thereof having an N-terminal deletion, operably linked to a tissue-specific promoter, wherein 161 amino acids as represented by SEQ ID NO: 10 are deleted at the N-terminus of the CDC27B polypeptide as represented by SEQ ID NO: 13, or by a homolog thereof having at least 95% amino acid sequence identity to SEQ ID NO: 13

2. The method of claim 1, wherein the CDC27B polypeptide or homolog thereof having an N-terminus deletion is encoded by the nucleic acid having GenBank accession number AC006081 (SEQ ID NO: 36).

3. The method of claim 1, wherein the CDC27B polypeptide or homolog thereof having an N-terminal deletion is a plant protein.

4. The method of claim 1, wherein the homolog thereof has at least 98% amino acid sequence identity to SEQ ID NO: 13.

5. A plant cell transformed with a vector comprising a nucleic acid encoding a CDC27B polypeptide or homolog thereof having an N-terminal deletion operably linked to a tissue-specific promoter, wherein 161 amino acids as represented by SEQ ID NO: 10 are deleted at the N-terminus of the CDC27B polypeptide as represented by SEQ ID NO: 13, or by a homolog thereof having at least 95% amino acid sequence identity to SEQ ID NO: 13.

6. The plant cell of claim 5, wherein the CDC27B polypeptide or homolog thereof having an N-terminus deletion is encoded by the nucleic acid having GenBank accession number AC006081 (SEQ ID NO: 36).

7. The plant cell of claim 5, wherein the CDC27B polypeptide or homolog thereof having an N-terminal deletion is a plant protein.

8. The plant cell of claim 5, wherein the homolog thereof has at least 98% amino acid sequence identity to SEQ ID NO: 13.

9. A method for modulating DNA replication in plant cells, plant parts or plants, comprising:

(i) transforming one or more plant cells with a nucleic acid encoding a CDC27B polypeptide or homolog thereof having an N-terminal deletion operably linked to a tissue-specific promoter active in the shoot apical meristem of a plant, wherein 161 amino acids as represented by SEQ ID NO: 10 are deleted at the N-terminus of the CDC27B polypeptide as represented by SEQ ID NO: 13, or by a homolog thereof having at least 95% amino acid sequence identity to SEQ ID NO: 13; and (ii) maintaining or culturing the plants cells to regenerate plant parts or plants from the transformed cells; and (iii) incubating the cells, plant parts or plants under conditions allowing the expression of the nucleic acid of(i) to produce a CDC27B polypeptide or homolog thereof having an N-terminal deletion, wherein 161 amino acids as represented by SEQ ID NO: 10 are deleted at the N-terminus of the CDC27B polypeptide as represented by SEQ ID NO: 13, or by a homolog thereof having at least 95% amino acid sequence identity to SEQ ID NO: 13.

10. The method of claim 9, wherein the homolog thereof has at least 98% amino acid sequence identity to SEQ ID NO: 13.

* * * * *

UNITED STATES PATENT AND TRADEMARK OFFICE

CERTIFICATE OF CORRECTION

PATENT NO. : 7,622,635 B2
APPLICATION NO. : 11/239325
DATED : November 24, 2009
INVENTOR(S) : Hemerly et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 355 days.

Signed and Sealed this

Twenty-sixth Day of October, 2010

David J. Kappos
*Director of the United States Patent and Trademark Office*

SEQUENCE LISTING

```
<160> NUMBER OF SEQ ID NOS: 35

<210> SEQ ID NO 1
<211> LENGTH: 889
<212> TYPE: PRT
<213> ORGANISM: Arabidopsis thaliana

<400> SEQUENCE: 1

Met Ser Glu Asn Ser Glu Pro Arg Gln Leu Glu Asn Ser Thr Ala Gly
1               5                   10                  15

Arg Glu Leu Ile Pro Leu Ser Pro Thr Asn Ser Asp Gly Asn Asp Asp
            20                  25                  30

Leu Asn Tyr His Leu His Ala Phe Glu Leu Ser Arg Leu Leu Leu Ser
        35                  40                  45

Ser Gly His Pro Glu Ser Val Ile Asp Leu Ser Ser Lys Cys Thr Tyr
    50                  55                  60

Phe Gln Gly Ser Pro Asn Leu Val Lys Tyr Leu Cys Ser Ile Pro Asn
65                  70                  75                  80

Ser Pro Ile Ser Leu Ala Glu Asp Gly Phe Thr Val Thr Leu Ser Pro
                85                  90                  95

Glu Ser Pro Ser Ala Pro Ala Ser Phe Ala Cys Ser Leu Asp Leu Gln
            100                 105                 110

Glu Asn Val Val Leu Glu Gln Phe Met Asp Pro Arg Ser Leu Thr Leu
        115                 120                 125

Lys His Ser Arg Glu Asn Ala Glu Gln Glu Glu Leu Glu Leu Met Pro
    130                 135                 140

Leu Pro Lys Arg Ser Arg Asn Asp Gly Asn Asp Val Asn Tyr Ser Val
145                 150                 155                 160

Ile Asp Ser Arg Pro Asn Asp Ile Arg Thr Val Ala Cys Gly Thr Met
                165                 170                 175

Leu Gly Thr Ile Leu Ala Leu Glu Ser Gln Ala Ser Val Phe Asn Leu
            180                 185                 190

Ser Ala Ser Asn Arg Gly Ile Glu Ala Phe Val Gln Asp His Gln Pro
        195                 200                 205

Gly Pro Gln Thr Ser Asn Ala Ser Val Asp Val Asn Pro Thr His Arg
    210                 215                 220

Leu Glu Glu Ser Lys Asn Asp Leu Pro Ser Pro Gln Glu Asp Gly Tyr
225                 230                 235                 240

Tyr Glu Arg Pro Glu Ile Gly Asp Phe Gln Ile Ala Asp Asn Gln Ile
                245                 250                 255

Leu Ile Glu Glu Gly Asp Asp Lys Asn Lys Lys Asp Leu Phe Pro Lys
            260                 265                 270

Gly Glu Ile Gln Thr Asp Ser Val Gln Ser Asp Pro Val Ala Ser Leu
        275                 280                 285

Met Pro Thr Glu Asn Glu Leu Glu Pro Val Gln Ile Val Asp Asp Thr
    290                 295                 300

Glu Asp Leu Leu Val Asp Asp His Thr Val Asp Ile Val Ser Thr Pro
305                 310                 315                 320

Asp Arg Glu Leu Pro Leu Lys Pro Ser Ala Thr Glu Ala Asn Gln Asp
```

-continued

```
                325                 330                 335

Lys Ser Leu Val Gln Lys Thr Leu Asp Gln Cys Lys Leu Pro Gly Asn
            340                 345                 350

Ser Lys Thr Tyr Ser Cys Ser Pro Glu Ile Lys His Thr Arg Lys Ser
        355                 360                 365

Lys Val Ile Gln Lys Arg Lys Gln Asn Phe Asn Thr Val Arg Leu Lys
    370                 375                 380

Asp Gln Lys Asp Gln Ala Lys His Asn Thr Ile Pro Asp Phe Asp Ser
385                 390                 395                 400

Tyr Thr Ile Val Glu Glu Glu Gly Ser Gly Gly Tyr Gly Ile Val Tyr
                405                 410                 415

Lys Ala Thr Arg Lys Thr Asp Gly Thr Glu Phe Ala Ile Lys Cys Pro
            420                 425                 430

His Val Gly Ala Gln Lys Tyr Tyr Val Asn Asn Glu Ile Arg Met Leu
        435                 440                 445

Glu Arg Phe Gly Gly Lys Asn Cys Ile Ile Lys His Glu Gly Cys Leu
    450                 455                 460

Lys Asn Gly Asp Ser Asp Cys Ile Ile Leu Glu His Leu Glu His Asp
465                 470                 475                 480

Arg Pro Asp Ser Leu Lys Arg Glu Ile Asp Val Tyr Gln Leu Gln Trp
                485                 490                 495

Tyr Gly Tyr Cys Met Phe Lys Ala Leu Ser Ser Leu His Lys Gln Gly
            500                 505                 510

Val Val His Arg Asp Val Lys Pro Gly Asn Phe Leu Phe Ser Arg Lys
        515                 520                 525

Thr Asn Lys Gly Tyr Leu Ile Asp Phe Asn Leu Ala Met Asp Leu His
    530                 535                 540

Gln Lys Tyr Arg Arg Ala Asp Lys Ser Lys Ala Ala Ser Gly Leu Pro
545                 550                 555                 560

Thr Ala Ser Lys Lys His His Thr Leu Val Lys Ser Leu Asp Ala Val
                565                 570                 575

Asn Arg Gly Thr Asn Lys Pro Ser Gln Lys Thr Leu Ala Pro Asn Ser
            580                 585                 590

Ile Lys Lys Ala Ala Gly Lys Thr Arg Ala Arg Asn Asp Met Thr Arg
        595                 600                 605

Trp Glu Arg Leu Asn Ser Gln Gly Ala Glu Gly Ser Gly Leu Thr Ser
    610                 615                 620

Ala Lys Asp Val Thr Ser Thr Arg Asn Asn Pro Ser Gly Glu Lys Arg
625                 630                 635                 640

Arg Glu Pro Leu Pro Cys His Gly Arg Lys Ala Leu Leu Asp Phe Leu
                645                 650                 655

Gln Glu Thr Met Ser Val Pro Ile Pro Asn His Glu Val Ser Ser Lys
            660                 665                 670

Ala Pro Thr Ser Met Arg Lys Arg Val Ala Ala Leu Pro Gly Lys Ala
        675                 680                 685

Glu Lys Glu Leu Leu Tyr Leu Thr Pro Met Pro Leu Cys Ser Asn Gly
    690                 695                 700

Arg Pro Glu Ala Gly Asp Val Ile Glu Lys Lys Asp Gly Pro Cys Ser
705                 710                 715                 720

Gly Thr Lys Gly Phe Arg Ala Pro Glu Val Cys Phe Arg Ser Leu His
                725                 730                 735

Gln Gly Pro Lys Ile Asp Val Trp Ser Ala Gly Val Thr Leu Leu Tyr
            740                 745                 750
```

-continued

```
Leu Ile Met Gly Arg Thr Pro Phe Thr Gly Asp Pro Glu Gln Asn Ile
        755                 760                 765

Lys Asp Ile Ala Gln Leu Arg Gly Ser Glu Glu Leu Trp Glu Val Ala
    770                 775                 780

Lys Leu His Asn Arg Glu Ser Ser Phe Pro Lys Glu Leu Tyr Glu Ser
785                 790                 795                 800

Arg Tyr Leu Lys Gly Met Glu Leu Arg Lys Trp Cys Glu Leu Asn Thr
                805                 810                 815

Lys Arg Arg Glu Phe Leu Asp Val Ile Pro Leu Ser Leu Leu Asp Leu
            820                 825                 830

Val Asp Lys Cys Leu Thr Val Asn Pro Arg Arg Arg Ile Ser Ala Glu
        835                 840                 845

Asp Ala Leu Lys His Asp Phe Phe His Pro Val His Glu Thr Leu Arg
    850                 855                 860

Asn Gln Met Leu Leu Lys Gln Gln Pro Thr Val Val Ala Asp Ala Val
865                 870                 875                 880

Ser Gln Thr Leu Asn Tyr Leu Gln Leu
                885


<210> SEQ ID NO 2
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 2

Gly Tyr Gly Ile Val Tyr Lys Ala Thr Arg Lys Thr Asp Gly Thr Glu
1               5                   10                  15

Phe Ala Ile Lys
            20


<210> SEQ ID NO 3
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 3

Asp Val Ile Glu Lys Lys Asp Gly Pro Cys Ser Gly Thr Lys Gly Phe
1               5                   10                  15

Arg Ala Pro Glu
            20


<210> SEQ ID NO 4
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 4

Asn Ile Lys Asp Ile Ala Gln Leu Arg Gly Ser Glu Glu Leu Trp Glu
1               5                   10                  15

Val Ala Lys Leu His Asn Arg Glu Ser Ser Phe Pro Lys
            20                  25


<210> SEQ ID NO 5
<211> LENGTH: 728
```

-continued

<212> TYPE: PRT
<213> ORGANISM: Arabidopsis thaliana

<400> SEQUENCE: 5

Met Met Glu Asn Leu Leu Ala Asn Cys Val Gln Lys Asn Leu Asn His
1               5                   10                  15

Phe Met Phe Thr Asn Ala Ile Phe Leu Cys Glu Leu Leu Leu Ala Gln
            20                  25                  30

Phe Pro Ser Glu Val Asn Leu Gln Leu Leu Ala Arg Cys Tyr Leu Ser
        35                  40                  45

Asn Ser Gln Ala Tyr Ser Ala Tyr Tyr Ile Leu Lys Gly Ser Lys Thr
    50                  55                  60

Pro Gln Ser Arg Tyr Leu Phe Ala Phe Ser Cys Phe Lys Leu Asp Leu
65                  70                  75                  80

Leu Gly Glu Ala Glu Ala Ala Leu Leu Pro Cys Glu Asp Tyr Ala Glu
                85                  90                  95

Glu Val Pro Gly Gly Ala Ala Gly His Tyr Leu Leu Gly Leu Ile Tyr
            100                 105                 110

Arg Tyr Ser Gly Arg Lys Asn Cys Ser Ile Gln Gln Phe Arg Met Ala
        115                 120                 125

Leu Ser Phe Asp Pro Leu Cys Trp Glu Ala Tyr Gly Glu Leu Cys Ser
    130                 135                 140

Leu Gly Ala Ala Glu Glu Ala Ser Thr Val Phe Gly Asn Val Ala Ser
145                 150                 155                 160

Gln Arg Leu Gln Lys Thr Cys Val Glu Gln Arg Ile Ser Phe Ser Glu
                165                 170                 175

Gly Ala Thr Ile Asp Gln Ile Thr Asp Ser Asp Lys Ala Leu Lys Asp
            180                 185                 190

Thr Gly Leu Ser Gln Thr Glu His Ile Pro Gly Glu Asn Gln Gln Asp
        195                 200                 205

Leu Lys Ile Met Gln Gln Pro Gly Asp Ile Pro Pro Asn Thr Asp Arg
    210                 215                 220

Gln Leu Ser Thr Asn Gly Trp Asp Leu Asn Thr Pro Ser Pro Val Leu
225                 230                 235                 240

Leu Gln Val Met Asp Ala Leu Pro Pro Leu Leu Leu Lys Asn Met Arg
                245                 250                 255

Arg Pro Ala Val Glu Gly Ser Leu Met Ser Val His Gly Val Arg Val
            260                 265                 270

Arg Arg Arg Asn Phe Phe Ser Glu Glu Leu Ser Ala Glu Ala Gln Glu
        275                 280                 285

Glu Ser Gly Arg Arg Arg Ser Ala Arg Ile Ala Ala Arg Lys Lys Asn
    290                 295                 300

Pro Met Ser Gln Ser Phe Gly Lys Asp Ser His Trp Leu His Leu Ser
305                 310                 315                 320

Pro Ser Glu Ser Asn Tyr Ala Pro Ser Leu Ser Ser Met Ile Gly Lys
                325                 330                 335

Cys Arg Ile Gln Ser Ser Lys Glu Val Ile Pro Asp Thr Val Thr Leu
            340                 345                 350

Asn Asp Pro Ala Thr Thr Ser Gly Gln Ser Val Ser Asp Ile Gly Ser
        355                 360                 365

Ser Val Asp Asp Glu Glu Lys Ser Asn Pro Ser Glu Ser Ser Pro Asp
    370                 375                 380

Arg Phe Ser Leu Ile Ser Gly Ile Ser Glu Val Leu Ser Leu Leu Lys
385                 390                 395                 400

-continued

```
Ile Leu Gly Asp Gly His Arg His Leu His Met Tyr Lys Cys Gln Glu
                405                 410                 415

Ala Leu Leu Ala Tyr Gln Lys Leu Ser Gln Lys Gln Tyr Asn Thr His
            420                 425                 430

Trp Val Leu Met Gln Val Gly Lys Ala Tyr Phe Glu Leu Gln Asp Tyr
        435                 440                 445

Phe Asn Ala Asp Ser Ser Phe Thr Leu Ala His Gln Lys Tyr Pro Tyr
    450                 455                 460

Ala Leu Glu Gly Met Asp Thr Tyr Ser Thr Val Leu Tyr His Leu Lys
465                 470                 475                 480

Glu Glu Met Arg Leu Gly Tyr Leu Ala Gln Glu Leu Ile Ser Val Asp
                485                 490                 495

Arg Leu Ser Pro Glu Ser Trp Cys Ala Val Gly Asn Cys Tyr Ser Leu
            500                 505                 510

Arg Lys Asp His Asp Thr Ala Leu Lys Met Phe Gln Arg Ala Ile Gln
        515                 520                 525

Leu Asn Glu Arg Phe Thr Tyr Ala His Thr Leu Cys Gly His Glu Phe
    530                 535                 540

Ala Ala Leu Glu Glu Phe Glu Asp Ala Glu Arg Cys Tyr Arg Lys Ala
545                 550                 555                 560

Leu Gly Ile Asp Thr Arg His Tyr Asn Ala Trp Tyr Gly Leu Gly Met
                565                 570                 575

Thr Tyr Leu Arg Gln Glu Lys Phe Glu Phe Ala Gln His Gln Phe Gln
            580                 585                 590

Leu Ala Leu Gln Ile Asn Pro Arg Ser Ser Val Ile Met Cys Tyr Tyr
        595                 600                 605

Gly Ile Ala Leu His Glu Ser Lys Arg Asn Asp Glu Ala Leu Met Met
    610                 615                 620

Met Glu Lys Ala Val Leu Thr Asp Ala Lys Asn Pro Leu Pro Lys Tyr
625                 630                 635                 640

Tyr Lys Ala His Ile Leu Thr Ser Leu Gly Asp Tyr His Lys Ala Gln
                645                 650                 655

Lys Val Leu Glu Glu Leu Lys Glu Cys Ala Pro Gln Glu Ser Ser Val
            660                 665                 670

His Ala Ser Leu Gly Lys Ile Tyr Asn Gln Leu Lys Gln Tyr Asp Lys
        675                 680                 685

Ala Val Leu His Phe Gly Ile Ala Leu Asp Leu Ser Pro Ser Pro Ser
    690                 695                 700

Asp Ala Val Lys Ile Lys Ala Tyr Met Glu Arg Leu Ile Leu Pro Asp
705                 710                 715                 720

Glu Leu Val Thr Glu Glu Asn Leu
                725
```

```
<210> SEQ ID NO 6
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 6

Val Asn Leu Gln Leu Leu Ala Arg Cys Tyr Leu Ser Asn Ser Gln Ala
1               5                   10                  15

Tyr Ser Ala Tyr Tyr Ile Leu Lys
            20
```

-continued

<210> SEQ ID NO 7
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 7

Ala Tyr Met Glu Arg Leu Ile Leu Pro Asp Glu Leu Val Thr Glu Glu
1               5                   10                  15

Asn Leu

<210> SEQ ID NO 8
<211> LENGTH: 2681
<212> TYPE: DNA
<213> ORGANISM: Arabidopsis thaliana

<400> SEQUENCE: 8
atgtcagaaa actcggaacc gcgtcaactc gagaattcta cagccggaag agagctcatt 60
cctcttagtc ccaccaattc agacggcaac gacgacctta actatcatct gcatgctttt 120
gagttatctc gtctcctact ttcttctggt catccagaat ctgttataga tctttcttca 180
aagtgtacat acttccaagg ttctcctaat ctcgtcaaat atctttgctc gatccctaat 240
tctcctattt cccttgccga agatggcttc actgtgactc tctcgcctga gtctccctcc 300
gctccggcta gtttcgcctg tagtttggat ttgcaggaaa atgttgtgtt agaacagttt 360
atggatccga gatctctcac gctaaagcat tcgagagaga atgcggaaca agaggagcta 420
gagctcatgc cattgcccaa aagaagtcga aatgatggaa acgatgtgaa ttactctgta 480
atagatagca gacctaacga catcagaact gttgcctgtg gaactatgct tgggactatt 540
ttagctcttg aatcccaagc ttcggttttc aatttaagtg catctaaccg aggaatagag 600
gcttttgttc aagatcatca gcctggtccg cagacatcca atgcttcagt ggatgtcaat 660
cctacacatc ggttagagga aagcaagaac gatttgccat ctcctcagga ggatggatat 720
tacgagcgac ctgaaattgg agatttccaa attgctgaca accaaatatt aatcgaagaa 780
ggtgatgata aaaataagaa ggatctcttc cctaagggag agatacaaac tgattctgtg 840
cagtccgatc ccgttgcctc attgatgcca acagaaaatg agttagaacc agtgcagatt 900
gtggatgaca ctgaagatct acttgtagat gatcacactg tagacatcgt tagcacccct 960
gacagagagc tgccgttgaa gccttctgct acagaagcta atcaagataa atctttggta 1020
caaaaaactc tggatcaatg caaattgccg ggaaacagca aaacgtacag ctgttcccct 1080
gagataaaac acaccagaaa aagtaaagtt atccagaaga ggaagcagaa ttttaacacc 1140
gttcgtctta aagatcagaa ggatcaggca aagcataaca caattccaga ttttgattct 1200
tacactattg tagaggaaga aggttcaggt ggctacggga ttgtttataa ggcaacgagg 1260
aaaactgatg gaacagagtt tgcaattaaa tgccctcatg ttggcgctca gaagtattat 1320
gtgaataatg aaatcagaat gctggagcgt tttgggggga aaaactgtat aataaagcat 1380
gaaggctgtc tcaagaatgg agattctgat tgcatcatcc ttgagcacct tgaacatgac 1440
agacctgatt cattgaagag agaaatagat gtgtatcagc tgcagtggta cggctactgc 1500
atgttcaaag ctctatcgag tctgcataag cagggtgttg ttcataggga tgttaagcca 1560
ggaaacttcc tcttctctag gaagaccaac aaaggctatc tcattgattt taaccttgcc 1620
atggatttgc accagaagta cagaagagca gataaatcaa aagcagcttc aggtcttcct 1680

-continued accgccagca agaaacatca tacattggtt aaatcactcg atgcggtaaa ccgagggacc 1740
aacaaacctt ctcagaaaac tttagcgcct aatagtatca agaaagcagc gggaaagaca 1800
agagctcgga atgacatgac cagatgggag agactcaata gccaaggggc agaagggtct 1860
ggcttaactt cagctaaaga tgtgaccagc acaaggaaca acccttcagg tgaaaagaga 1920
agagagcctt tgccatgtca tggaagaaaa gcgcttttag attttctgca agagacaatg 1980
tctgttccaa ttccaaacca tgaagtatca tccaaagctc ctacgtctat gagaaaacgg 2040
gtagctgctc ttccagggaa agctgagaag gaacttcttt atctgacccc aatgccactg 2100
tgctctaacg gtcggcctga agcaggggac gtaattgaga agaaagacgg tccttgctca 2160
ggaaccaaag gcttccgagc tccagaggtt tgcttcagat ctttgcacca aggacctaag 2220
atagacgtgt ggtctgcggg agttactttg ttatacctca taatgggaag gacacctttc 2280
actggtgacc ctgaacagaa cataaaggac attgcacaac tacgaggcag tgaagaatta 2340
tgggaagtag ccaagctgca caaccgtgaa tcctctttcc ctaaggaatt atacgagtca 2400
aggtacttga aggggatgga gttgagaaaa tggtgcgaac tcaacacaaa acgcagagag 2460
tttctagacg taattccact atcgcttctt gacctcgttg ataaatgttt gaccgttaac 2520
ccgaggcgac gaatcagcgc agaggatgct ctcaagcacg acttcttcca tccagtacat 2580
gaaaccctta gaaaccaaat gctccttaaa cagcagccta cagtggttgc tgacgcagta 2640
agccaaactc taaactattt acaattgtaa aagtaaataa g 2681

<210> SEQ ID NO 9
<211> LENGTH: 2434
<212> TYPE: DNA
<213> ORGANISM: Arabidopsis thaliana

<400> SEQUENCE: 9
atgatggaga atctactggc gaattgtgtc cagaaaaacc ttaaccattt tatgttcacc 60
aatgctatct tcctttgcga acttcttctc gcccaatttc catctgaggt gaacctgcaa 120
ttgttagcca ggtgttactt gagtaacagt caagcttata gtgcatatta tatccttaaa 180
ggttcaaaaa cgcctcagtc tcggtattta tttgcattct catgctttaa gttggatctt 240
cttggagagg ctgaagctgc attgttgccc tgtgaagatt atgctgaaga agttcctggt 300
ggtgcagctg ggcattatct tcttggtctt atatatagat attctgggag gaagaactgt 360
tcaatacaac agtttaggat ggcattgtca tttgatccat tgtgttggga agcatatgga 420
gaactttgta gtttaggtgc cgctgaagaa gcctcaacag ttttcgggaa tgttgcttcc 480
cagcgtctta aaacttgtgt agaacaaaga ataagcttct cagaaggagc aaccatagac 540
cagattacag attctgataa ggccttaaaa gatacaggtt tatcgcaaac agaacacatt 600
ccaggagaga accaacaaga tctgaaaatt atgcagcagc ctggagatat tccaccaaat 660
actgacaggc aacttagtac aaacggatgg gacttgaaca caccttctcc agtgctttta 720
caggtaatgg atgctccacc gcctctgctt cttaagaata tgcgtcgtcc agcagtggaa 780
ggatctttga tgtctgtaca tggagtgcgt gtgcgtcgaa gaaacttttt tagtgaagaa 840
ttgtcagcag aggctcaaga agaatctggg cgccgccgta gtgctagaat agcagcaagg 900
aaaaagaatc ctatgtcgca gtcatttgga aaagattccc attggttaca tctttcacct 960
tccgagtcaa actatgcacc ttctctttcc tcgatgattg gaaaatgcag aatccaaagc 1020
agcaaagaag cgattcctga taccgttact ctaaatgatc cagcaacgac gtcaggccag 1080

-continued

```
tctgtaagtg acactggaag ctctgttgat gatgaggaaa agtcaaatcc tagtgaatct   1140

tccccggatc gtttcagcct tatttctgga atttcagaag tgctaggcat tctgaaaatt   1200

cttggagatg gccacaggca tttacatatg tacaagtgtc aggaagcttt gttggcatat   1260

caaaagctat ctcagaaaca atacaataca cactgggttc tcatgcaggt tggaaaagca   1320

tattttgagc tacaagacta cttcaacgct gactcttcct ttactcttgc tcatcaaaag   1380

tatccttatg ctttggaagg aatggataca tactccactg ttctttatca cctgaaagaa   1440

gagatgaggt tgggctatct ggctcaggaa ctgatttcag ttgatcgcct gtctccagaa   1500

tcctggtgtg cagttgggaa ctgttacagt ttgcgtaagg atcatgatac tgctctcaaa   1560

atgtttcaga gagctatcca actgaatgaa agattcacat atgcacatac cctttgtggc   1620

cacgagtttg ccgcattgga agaattcgag gatgcagaga gatgctaccg gaaggctctg   1680

ggcatagata cgagacacta taatgcatgg tacggtcttg gaatgaccta tcttcgtcag   1740

gagaaattcg agtttgcgca gcatcaattt caactggctc tccaaataaa tccaagatct   1800

tcagtcatca tgtgttacta tggaattgct ttgcatgagt caaagagaaa cgatgaggcg   1860

ttgatgatga tggagaaggc tgtactcact gatgcaaaga atccgctccc caagtactac   1920

aaggctcaca tattaaccag cctaggtgat tatcacaaag cacagaaagt tttagaagag   1980

ctcaaagaat gtgctcctca agaaagcagt gtccatgcat cgcttggcaa aatatacaat   2040

cagctaaagc aatacgacaa agccgtgtta catttcggca ttgctttgga tttaagccct   2100

tctccatctg atgctgtcaa gataaaggct tacatggaga ggttgatact accagacgag   2160

ctggtgacgg aggaaaattt gtagatttat tgtgcaggta atacaccaga ttatgtttct   2220

catataaccc aaagtcatct gtaatttttc tcatctttag atcagtcttg tggactaacc   2280

ctaaaacaaa actgattata taaacttaga gggtaatatt acagaaaatt gtatagagtt   2340

gggtttgaat tttcatttct tttccaagtt ggaacttttg ttcaaaaaaa aaaaaaaaaa   2400

aaaaaaaaaa aaaaaaaaaa aaaaaaaaaa aaaa                               2434


<210> SEQ ID NO 10
<211> LENGTH: 161
<212> TYPE: PRT
<213> ORGANISM: Artificial Sequence
<220> FEATURE:
<223> OTHER INFORMATION: Synthetic Peptide

<400> SEQUENCE: 10

Met Glu Ala Met Leu Val Asp Cys Val Asn Asn Ser Leu Arg His Phe
1               5                   10                  15

Val Tyr Lys Asn Ala Ile Phe Met Cys Glu Arg Leu Cys Ala Glu Phe
            20                  25                  30

Pro Ser Glu Val Asn Leu Gln Leu Leu Ala Thr Ser Tyr Leu Gln Asn
        35                  40                  45

Asn Gln Ala Tyr Ser Ala Tyr His Leu Leu Lys Gly Thr Gln Met Ala
    50                  55                  60

Gln Ser Arg Tyr Leu Phe Ala Leu Ser Cys Phe Gln Met Asp Leu Leu
65                  70                  75                  80

Asn Glu Ala Glu Ser Ala Leu Cys Pro Val Asn Glu Pro Gly Ala Glu
                85                  90                  95

Ile Pro Asn Gly Ala Ala Gly His Tyr Leu Leu Gly Leu Ile Tyr Lys
            100                 105                 110

Lys Asn Ala Ala Gln Gln Phe Lys Gln Ser Leu Thr Ile Asp Pro Leu
        115                 120                 125
```

-continued

```
Leu Trp Ala Ala Tyr Glu Glu Leu Cys Ile Leu Gly Ala Ala Glu Glu
    130                 135                 140

Ala Thr Ala Val Phe Gly Glu Thr Ala Ala Leu Ser Ile Gln Lys Gln
145                 150                 155                 160

Tyr


<210> SEQ ID NO 11
<211> LENGTH: 716
<212> TYPE: PRT
<213> ORGANISM: Arabidopsis thaliana

<400> SEQUENCE: 11

Met Met Glu Asn Leu Leu Ala Asn Cys Val Gln Lys Asn Leu Asn His
1               5                   10                  15

Phe Met Phe Thr Asn Ala Ile Phe Leu Cys Glu Leu Leu Leu Ala Gln
            20                  25                  30

Phe Pro Ser Glu Val Asn Leu Gln Leu Leu Ala Arg Cys Tyr Leu Ser
        35                  40                  45

Asn Ser Gln Ala Tyr Ser Ala Tyr Tyr Ile Leu Lys Gly Ser Lys Thr
    50                  55                  60

Pro Gln Ser Arg Tyr Leu Phe Ala Phe Ser Cys Phe Lys Leu Asp Leu
65                  70                  75                  80

Leu Gly Glu Ala Glu Ala Ala Leu Leu Pro Cys Glu Asp Tyr Ala Glu
                85                  90                  95

Glu Val Pro Gly Gly Ala Ala Gly His Tyr Leu Leu Gly Leu Ile Tyr
            100                 105                 110

Arg Tyr Ser Gly Arg Lys Asn Cys Ser Ile Gln Gln Phe Arg Met Ala
        115                 120                 125

Leu Ser Phe Asp Pro Leu Cys Trp Glu Ala Tyr Gly Glu Leu Cys Ser
    130                 135                 140

Leu Gly Ala Ala Glu Glu Ala Ser Thr Val Phe Gly Asn Val Ala Ser
145                 150                 155                 160

Gln Arg Leu Lys Thr Cys Val Glu Gln Arg Ile Ser Phe Ser Glu Gly
                165                 170                 175

Ala Thr Ile Asp Gln Ile Thr Asp Ser Asp Lys Ala Leu Lys Asp Thr
            180                 185                 190

Gly Leu Ser Gln Thr Glu His Ile Pro Gly Glu Asn Gln Gln Asp Leu
        195                 200                 205

Lys Ile Met Gln Gln Pro Gly Asp Ile Pro Pro Asn Thr Asp Arg Gln
    210                 215                 220

Leu Ser Thr Asn Gly Trp Asp Leu Asn Thr Pro Ser Pro Val Leu Leu
225                 230                 235                 240

Gln Val Met Asp Ala Pro Pro Pro Leu Leu Leu Lys Asn Met Arg Arg
                245                 250                 255

Pro Ala Val Glu Gly Ser Leu Met Ser Val His Gly Val Arg Val Arg
            260                 265                 270

Arg Arg Asn Phe Phe Ser Glu Glu Leu Ser Ala Glu Ala Gln Glu Glu
        275                 280                 285

Ser Gly Arg Arg Arg Ser Ala Arg Ile Ala Ala Arg Lys Lys Asn Pro
    290                 295                 300

Met Ser Gln Ser Phe Gly Lys Asp Ser His Trp Leu His Leu Ser Pro
305                 310                 315                 320

Ser Glu Ser Asn Tyr Ala Pro Ser Leu Ser Ser Met Ile Gly Lys Cys
                325                 330                 335
```

-continued

Arg Ile Gln Ser Ser Lys Glu Ala Thr Thr Ser Gly Gln Ser Val Ser
340 345 350

Asp Thr Gly Ser Ser Val Asp Asp Glu Glu Lys Ser Asn Pro Ser Glu
355 360 365

Ser Ser Pro Asp Arg Phe Ser Leu Ile Ser Gly Ile Ser Glu Val Leu
370 375 380

Ser Ile Leu Lys Ile Leu Gly Asp Gly His Arg His Leu His Met Tyr
385 390 395 400

Lys Cys Gln Glu Ala Leu Leu Ala Tyr Gln Lys Leu Ser Gln Lys Gln
405 410 415

Tyr Asn Thr His Trp Val Leu Met Gln Val Gly Lys Ala Tyr Phe Glu
420 425 430

Leu Gln Asp Tyr Phe Asn Ala Asp Ser Ser Phe Thr Leu Ala His Gln
435 440 445

Lys Tyr Pro Tyr Ala Leu Glu Gly Met Asp Thr Tyr Ser Thr Val Leu
450 455 460

Tyr His Leu Lys Glu Glu Met Arg Leu Gly Tyr Leu Ala Gln Glu Leu
465 470 475 480

Ile Ser Val Asp Arg Leu Ser Pro Glu Ser Trp Cys Ala Val Gly Asn
485 490 495

Cys Tyr Ser Leu Arg Lys Asp His Asp Thr Ala Leu Lys Met Phe Gln
500 505 510

Arg Ala Ile Gln Leu Asn Glu Arg Phe Thr Tyr Ala His Thr Leu Cys
515 520 525

Gly His Glu Phe Ala Ala Leu Glu Glu Phe Glu Asp Ala Glu Arg Cys
530 535 540

Tyr Arg Lys Ala Leu Gly Ile Asp Thr Arg His Tyr Asn Ala Trp Tyr
545 550 555 560

Gly Leu Gly Met Thr Tyr Leu Arg Gln Glu Lys Phe Glu Phe Ala Gln
565 570 575

His Gln Phe Gln Leu Ala Leu Gln Ile Asn Pro Arg Ser Ser Val Ile
580 585 590

Met Cys Tyr Tyr Gly Ile Ala Leu His Glu Ser Lys Arg Asn Asp Glu
595 600 605

Ala Leu Met Met Met Glu Lys Ala Val Leu Thr Asp Ala Lys Asn Pro
610 615 620

Leu Pro Lys Tyr Tyr Lys Ala His Ile Leu Thr Ser Leu Gly Asp Tyr
625 630 635 640

His Lys Ala Gln Lys Val Leu Glu Glu Leu Lys Glu Cys Ala Pro Gln
645 650 655

Glu Ser Ser Val His Ala Ser Leu Gly Lys Ile Tyr Asn Gln Leu Lys
660 665 670

Gln Tyr Asp Lys Ala Val Leu His Phe Gly Ile Ala Leu Asp Leu Ser
675 680 685

Pro Ser Pro Ser Asp Ala Val Lys Ile Lys Ala Tyr Met Glu Arg Leu
690 695 700

Ile Leu Pro Asp Glu Leu Val Thr Glu Glu Asn Leu
705 710 715

<210> SEQ ID NO 12
<211> LENGTH: 12
<212> TYPE: PRT
<213> ORGANISM: Artificial Sequence
<220> FEATURE:

-continued

<223> OTHER INFORMATION: Synthetic Peptide

<400> SEQUENCE: 12

Ala Ile Pro Asp Thr Val Thr Leu Asn Asp Pro Ala
1 5 10

<210> SEQ ID NO 13
<211> LENGTH: 739
<212> TYPE: PRT
<213> ORGANISM: Arabidopsis thaliana

<400> SEQUENCE: 13

Met Glu Ala Met Leu Val Asp Cys Val Asn Asn Ser Leu Arg His Phe
1 5 10 15

Val Tyr Lys Asn Ala Ile Phe Met Cys Glu Arg Leu Cys Ala Glu Phe
20 25 30

Pro Ser Glu Val Asn Leu Gln Leu Leu Ala Thr Ser Tyr Leu Gln Asn
35 40 45

Asn Gln Ala Tyr Ser Ala Tyr His Leu Leu Lys Gly Thr Gln Met Ala
50 55 60

Gln Ser Arg Tyr Leu Phe Ala Leu Ser Cys Phe Gln Met Asp Leu Leu
65 70 75 80

Asn Glu Ala Glu Ser Ala Leu Cys Pro Val Asn Glu Pro Gly Ala Glu
85 90 95

Ile Pro Asn Gly Ala Ala Gly His Tyr Leu Leu Gly Leu Ile Tyr Lys
100 105 110

Lys Asn Ala Ala Gln Gln Phe Lys Gln Ser Leu Thr Ile Asp Pro Leu
115 120 125

Leu Trp Ala Ala Tyr Glu Glu Leu Cys Ile Leu Gly Ala Ala Glu Glu
130 135 140

Ala Thr Ala Val Phe Gly Glu Thr Ala Ala Leu Ser Ile Gln Lys Gln
145 150 155 160

Tyr Met Gln Gln Leu Ser Thr Ser Leu Gly Leu Asn Thr Tyr Asn Glu
165 170 175

Glu Arg Asn Ser Thr Ser Thr Lys Asn Thr Ser Ser Glu Asp Tyr Ser
180 185 190

Pro Arg Gln Ser Lys His Thr Gln Ser His Gly Leu Lys Asp Ile Ser
195 200 205

Gly Asn Phe His Ser His Gly Val Asn Gly Gly Val Ser Asn Met Ser
210 215 220

Phe Tyr Asn Thr Pro Ser Pro Val Ala Ala Gln Leu Ser Gly Ile Ala
225 230 235 240

Pro Pro Pro Leu Phe Arg Asn Phe Gln Pro Ala Val Ala Asn Pro Asn
245 250 255

Ser Leu Ile Thr Asp Ser Ser Pro Lys Ser Thr Val Asn Ser Thr Leu
260 265 270

Gln Ala Pro Arg Arg Lys Phe Val Asp Glu Gly Lys Leu Arg Lys Ile
275 280 285

Ser Gly Arg Leu Phe Ser Asp Ser Gly Pro Arg Arg Ser Ser Arg Leu
290 295 300

Ser Ala Asp Ser Gly Ala Asn Ile Asn Ser Ser Val Ala Thr Val Ser
305 310 315 320

Gly Asn Val Asn Asn Ala Ser Lys Tyr Leu Gly Gly Ser Lys Leu Ser
325 330 335

Ser Leu Ala Leu Arg Ser Val Thr Leu Arg Lys Gly His Ser Trp Ala

-continued

```
        340                 345                 350

Asn Glu Asn Met Asp Glu Gly Val Arg Gly Glu Pro Phe Asp Asp Ser
    355                 360                 365

Arg Pro Asn Thr Ala Ser Thr Thr Gly Ser Met Ala Ser Asn Asp Gln
    370                 375                 380

Glu Asp Glu Thr Met Ser Ile Gly Gly Ile Ala Met Ser Ser Gln Thr
385                 390                 395                 400

Ile Thr Ile Gly Val Ser Glu Ile Leu Asn Leu Leu Arg Thr Leu Gly
                405                 410                 415

Glu Gly Cys Arg Leu Ser Tyr Met Tyr Arg Cys Gln Glu Ala Leu Asp
            420                 425                 430

Thr Tyr Met Lys Leu Pro His Lys His Tyr Asn Thr Gly Trp Val Leu
        435                 440                 445

Ser Gln Val Gly Lys Ala Tyr Phe Glu Leu Ile Asp Tyr Leu Glu Ala
    450                 455                 460

Glu Lys Ala Phe Arg Leu Ala Arg Leu Ala Ser Pro Tyr Cys Leu Glu
465                 470                 475                 480

Gly Met Asp Ile Tyr Ser Thr Val Leu Tyr His Leu Lys Glu Asp Met
                485                 490                 495

Lys Leu Ser Tyr Leu Ala Gln Glu Leu Ile Ser Thr Asp Arg Leu Ala
            500                 505                 510

Pro Gln Ser Trp Cys Ala Met Gly Asn Cys Tyr Ser Leu Gln Lys Asp
        515                 520                 525

His Glu Thr Ala Leu Lys Asn Phe Leu Arg Ala Val Gln Leu Asn Pro
    530                 535                 540

Arg Phe Ala Tyr Ala His Thr Leu Cys Gly His Glu Tyr Thr Thr Leu
545                 550                 555                 560

Glu Asp Phe Glu Asn Gly Met Lys Ser Tyr Gln Asn Ala Leu Arg Val
                565                 570                 575

Asp Thr Arg His Tyr Asn Ala Trp Tyr Gly Leu Gly Met Ile Tyr Leu
            580                 585                 590

Arg Gln Glu Lys Leu Glu Phe Ser Glu His His Phe Arg Met Ala Phe
        595                 600                 605

Leu Ile Asn Pro Ser Ser Ser Val Ile Met Ser Tyr Leu Gly Thr Ser
    610                 615                 620

Leu His Ala Leu Lys Arg Ser Glu Glu Ala Leu Glu Ile Met Glu Gln
625                 630                 635                 640

Ala Ile Val Ala Asp Arg Lys Asn Pro Leu Pro Met Tyr Gln Lys Ala
                645                 650                 655

Asn Ile Leu Val Cys Leu Glu Arg Leu Asp Glu Ala Leu Glu Val Leu
            660                 665                 670

Glu Glu Leu Lys Glu Tyr Ala Pro Ser Glu Ser Ser Val Tyr Ala Leu
        675                 680                 685

Met Gly Arg Ile Tyr Lys Arg Arg Asn Met His Asp Lys Ala Met Leu
    690                 695                 700

His Phe Gly Leu Ala Leu Asp Met Lys Pro Pro Ala Thr Asp Val Ala
705                 710                 715                 720

Ala Ile Lys Ala Ala Met Glu Lys Leu His Val Pro Asp Glu Ile Asp
                725                 730                 735

Glu Ser Pro

<210> SEQ ID NO 14
<211> LENGTH: 2401
```

-continued

<212> TYPE: DNA
<213> ORGANISM: Arabidopsis thaliana

<400> SEQUENCE: 14
atgatggaga atctactggc gaattgtgtc cagaaaaacc ttaaccattt tatgttcacc 60
aatgctatct tcctttgcga acttcttctc gcccaatttc catctgaggt gaacctgcaa 120
ttgttagcca ggtgttactt gagtaacagt caagcttata gtgcatatta tatccttaaa 180
ggttcaaaaa cgcctcagtc tcggtattta tttgcattct catgctttaa gttggatctt 240
cttggagagg ctgaagctgc attgttgccc tgtgaagatt atgctgaaga agttcctggt 300
ggtgcagctg ggcattatct tcttggtctt atatatagat attctgggag gaagaactgt 360
tcaatacaac agtttaggat ggcattgtca tttgatccat tgtgttggga agcatatgga 420
gaactttgta gtttaggtgc cgctgaagaa gcctcaacag ttttcgggaa tgttgcttcc 480
cagcgtctta aaacttgtgt agaacaaaga ataagcttct cagaaggagc aaccatagac 540
cagattacag attctgataa ggccttaaaa gatacaggtt tatcgcaaac agaacacatt 600
ccaggagaga accaacaaga tctgaaaatt atgcagcagc ctggagatat tccaccaaat 660
actgacaggc aacttagtac aaacggatgg gacttgaaca caccttctcc agtgctttta 720
caggtaatgg atgctccacc gcctctgctt cttaagaata tgcgtcgtcc agcagtggaa 780
ggatctttga tgtctgtaca tggagtgcgt gtgcgtcgaa gaaacttttt tagtgaagaa 840
ttgtcagcag aggctcaaga agaatctggg cgccgccgta gtgctagaat agcagcaagg 900
aaaaagaatc ctatgtcgca gtcatttgga aaagattccc attggttaca tctttcacct 960
tccgagtcaa actatgcacc ttctctttcc tcgatgattg gaaaatgcag aatccaaagc 1020
agcaaagaag caacgacgtc aggccagtct gtaagtgaca ctggaagctc tgttgatgat 1080
gaggaaaagt caaatcctag tgaatcttcc ccggatcgtt tcagccttat ttctggaatt 1140
tcagaagtgc taagcattct gaaaattctt ggagatggcc acaggcattt acatatgtac 1200
aagtgtcagg aagctttgtt ggcatatcaa aagctatctc agaaacaata caatacacac 1260
tgggttctca tgcaggttgg aaaagcatat tttgagctac aagactactt caacgctgac 1320
tcttccttta ctcttgctca tcaaaagtat ccttatgctt tggaaggaat ggatacatac 1380
tccactgttc tttatcacct gaaagaagag atgaggttgg gctatctggc tcaggaactg 1440
atttcagttg atcgcctgtc tccagaatcc tggtgtgcag ttgggaactg ttacagtttg 1500
cgtaaggatc atgatactgc tctcaaaatg tttcagagag ctatccaact gaatgaaaga 1560
ttcacatatg cacataccct ttgtggccac gagtttgccg cattggaaga attcgaggat 1620
gcagagagat gctaccggaa ggctctgggc atagatacga gacactataa tgcatggtac 1680
ggtcttggaa tgacctatct tcgtcaggag aaattcgagt ttgcgcagca tcaatttcaa 1740
ctggctctcc aaataaatcc aagatcttca gtcatcatgt gttactatgg aattgctttg 1800
catgagtcaa agagaaacga tgaggcgttg atgatgatgg agaaggctgt actcactgat 1860
gcaaagaatc cgctccccaa gtactacaag gctcacatat taaccagcct aggtgattat 1920
cacaaagcac agaaagtttt agaagagctc aaagaatgtg ctcctcaaga aagcagtgtc 1980
catgcatcgc ttggcaaaat atacaatcag ctaaagcaat acgacaaagc cgtgttacat 2040
ttcggcattg ctttggattt aagcccttct ccatctgatg ctgtcaagat aaaggcttac 2100
atggagaggt tgatactacc agacgagctg gtgacggagg aaaatttgta gatttattgt 2160
gcaggtaata caccagatta tgtttctcat ataacccaaa gtcatctgta atttttctca 2220

-continued

```
tctttagatc agtcttgtgg actaacccta aaacaaaact gattatataa acttagaggg   2280

taatattaca gaaaattgta tagagttggg tttgaatttt catttctttt ccaagttgga   2340

acttttgttc aaaaaaaaaa aaaaaaaaaa aaaaaaaaaa aaaaaaaaaa aaaaaaaaaa   2400

a                                                                   2401
```

<210> SEQ ID NO 15
<211> LENGTH: 2220
<212> TYPE: DNA
<213> ORGANISM: Arabidopsis thaliana

<400> SEQUENCE: 15

```
atggaagcta tgcttgtgga ctgtgtaaac aacagtcttc gtcattttgt ctacaaaaat     60

gctattttca tgtgcgagcg tctctgcgct gagtttcctt ctgaggttaa tttgcagcta    120

ttagccacca gctacctgca gaataatcaa gcttacagtg catatcatct gctaaaggga    180

acacaaatgg ctcagtcccg atacttgttc gcattatcat gcttccagat ggaccttctc    240

aatgaagctg aatctgcact ctgccctgtt aatgaacctg gtgcggagat cccaaatggt    300

gcagcaggcc attaccttct tggacttatt tacaagaaga atgctgctca acaatttaaa    360

cagtccttga caatagaccc tctactttgg gctgcatatg aggaattatg tatattaggt    420

gctgctgagg aagcaactgc agtttttggt gaaacagctg ctctctccat tcaaaagcag    480

tatatgcaac aactgtcaac ttccctcggc ttaaacactt acaacgagga acgtaattca    540

acttctacta aaaacacgag ttctgaagat tatagtccaa ggcagtctaa acacacacaa    600

agccatggcc ttaaagatat ctccggaaat ttccattctc atggagttaa tggaggtgtt    660

tcgaacatgt cattctataa tacgccttcg ccagtggctg cacagctatc cggtatagct    720

ccaccaccac ttttccggaa ttttcagcca gctgttgcaa acccaaactc ccttattact    780

gacagttctc caaagtccac tgttaactct actcttcaag cacctagaag aaagtttgta    840

gatgaaggaa agttacgtaa gatttctggc agactatttt ctgattctgg tccacgacgg    900

agttcaagac tgtctgctga ttcaggggca aacattaatt caagtgttgc aacagtaagc    960

ggaaatgtga acaacgcttc caagtatttg ggaggttcta aattgagttc tttggcactt   1020

cgttctgtaa cacttcggaa gggacactcc tgggcaaatg aaaacatgga tgaaggggtc   1080

cgtggggaac cttttgatga ttcaaggcct aatactgcct caacgactgg ttctatggct   1140

tccaatgatc aagaagacga aacaatgtcg attggtggca tagcaatgag ttctcaaaca   1200

atcacaattg gtgtttcgga aattttaaac ctccttagga cactcggaga agggtgtaga   1260

ctttcataca tgtacaggtg tcaggaggca ctggatacgt atatgaaact tccacataag   1320

cattataata caggatgggt tctttcccag gtcgggaaag catactttga actaattgac   1380

tatttagagg ctgaaaaggc attccgtctt gcccgtctgg cttctcctta ttgcttagaa   1440

ggaatggata tatactctac ggtcctctat catttgaagg aagacatgaa gctgagttac   1500

ttggctcagg aactaatatc aaccgatcgc ttagctcctc aatcttggtg tgctatggga   1560

aattgctata gcttgcaaaa ggaccatgag accgcactga agaatttcct acgagctgtt   1620

caactgaatc caagatttgc atatgcacat accttatgtg gccacgaata cacaactctt   1680

gaggattttg agaacggaat gaaaagttac caaaacgcac ttcgtgtaga tacaagacac   1740

tacaacgcat ggtacgggct tggaatgata tatctacgcc aagagaagtt agagttctca   1800

gagcatcact tcagaatggc tttcctaata aacccgagtt cctctgttat aatgtcttat   1860

ttagggacat ctttgcatgc cttgaagaga agtgaggaag cactagagat aatggagcaa   1920
```

-continued

```
gccatagtag cagatagaaa aaaccctctt ccaatgtacc agaaagctaa catacttgtc   1980

tgcttagaaa gattagatga agctctagaa gttcttgagg agctcaaaga gtatgcgcct   2040

tcagagagca gcgtttacgc tttaatgggc aggatctata agcggcgaaa catgcacgat   2100

aaagccatgc ttcatttcgg tctagcttta gatatgaaac cgcctgcaac tgacgttgct   2160

gcaataaagg ctgcaatgga gaaattgcat gttccagatg agatcgatga gagcccgtga   2220


<210> SEQ ID NO 16
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(3)
<223> OTHER INFORMATION: X = any amino acid
<220> FEATURE:
<221> NAME/KEY: MISC_FEATURE
<222> LOCATION: (5)..(6)
<223> OTHER INFORMATION: X = any amino acid
<220> FEATURE:
<221> NAME/KEY: MISC_FEATURE
<222> LOCATION: (9)..(10)
<223> OTHER INFORMATION: X = any amino acid
<220> FEATURE:
<221> NAME/KEY: MISC_FEATURE
<222> LOCATION: (12)..(19)
<223> OTHER INFORMATION: X = any amino acid
<220> FEATURE:
<221> NAME/KEY: MISC_FEATURE
<222> LOCATION: (21)..(23)
<223> OTHER INFORMATION: X = any amino acid
<220> FEATURE:
<221> NAME/KEY: MISC_FEATURE
<222> LOCATION: (25)..(26)
<223> OTHER INFORMATION: X = any amino acid
<220> FEATURE:
<221> NAME/KEY: MISC_FEATURE
<222> LOCATION: (28)..(31)
<223> OTHER INFORMATION: X = any amino acid
<220> FEATURE:
<221> NAME/KEY: MISC_FEATURE
<222> LOCATION: (33)..(34)
<223> OTHER INFORMATION: X = any amino acid

<400> SEQUENCE: 16

Xaa Xaa Xaa Trp Xaa Xaa Leu Gly Xaa Xaa Tyr Xaa Xaa Xaa Xaa Xaa
1               5                   10                  15

Xaa Xaa Xaa Ala Xaa Xaa Xaa Phe Xaa Xaa Ala Xaa Xaa Xaa Xaa Pro
            20                  25                  30

Xaa Xaa


<210> SEQ ID NO 17
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 17

Thr Lys Gly Phe Arg Ala Pro Glu
1               5


<210> SEQ ID NO 18
<211> LENGTH: 20
<212> TYPE: DNA
<213> ORGANISM: Artificial Sequence
```

-continued

<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n = a, c, g, or t
<220> FEATURE:
<221> NAME/KEY: misc_feature
<222> LOCATION: (15)..(15)
<223> OTHER INFORMATION: n = a, c, g, or t
<220> FEATURE:
<221> NAME/KEY: misc_feature
<222> LOCATION: (18)..(18)
<223> OTHER INFORMATION: n = a, c, g, or t

<400> SEQUENCE: 18
aarathggng arggnacntt 20

<210> SEQ ID NO 19
<211> LENGTH: 20
<212> TYPE: DNA
<213> ORGANISM: Artificial Sequence
<220> FEATURE:
<223> OTHER INFORMATION: Synthetic DNA

<400> SEQUENCE: 19
athathcaya grgarathaa 20

<210> SEQ ID NO 20
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n = a, c, g, or t
<220> FEATURE:
<221> NAME/KEY: misc_feature
<222> LOCATION: (9)..(9)
<223> OTHER INFORMATION: n = a, c, g, or t
<220> FEATURE:
<221> NAME/KEY: misc_feature
<222> LOCATION: (18)..(18)
<223> OTHER INFORMATION: n = a, c, g, or t

<400> SEQUENCE: 20
agytcnggng cyctraancc 20

<210> SEQ ID NO 21
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (3)..(3)
<223> OTHER INFORMATION: n = a, c, g, or t
<220> FEATURE:
<221> NAME/KEY: misc_feature
<222> LOCATION: (6)..(6)
<223> OTHER INFORMATION: n = a, c, g, or t
<220> FEATURE:
<221> NAME/KEY: misc_feature
<222> LOCATION: (15)..(15)
<223> OTHER INFORMATION: n = a, c, g, or t

<400> SEQUENCE: 21
acnccnrcrc tccanatrtc 20

-continued

<210> SEQ ID NO 22
<211> LENGTH: 19
<212> TYPE: DNA
<213> ORGANISM: Artificial Sequence
<220> FEATURE:
<223> OTHER INFORMATION: Synthetic DNA

<400> SEQUENCE: 22
ccgtagtgct agaatagca 19

<210> SEQ ID NO 23
<211> LENGTH: 16
<212> TYPE: DNA
<213> ORGANISM: Artificial Sequence
<220> FEATURE:
<223> OTHER INFORMATION: Synthetic DNA

<400> SEQUENCE: 23
agtcagcgtt gaagtc 16

<210> SEQ ID NO 24
<211> LENGTH: 24
<212> TYPE: DNA
<213> ORGANISM: Artificial Sequence
<220> FEATURE:
<223> OTHER INFORMATION: Synthetic DNA

<400> SEQUENCE: 24
tctctcgagg aagaaaggca acaa 24

<210> SEQ ID NO 25
<211> LENGTH: 24
<212> TYPE: DNA
<213> ORGANISM: Artificial Sequence
<220> FEATURE:
<223> OTHER INFORMATION: Synthetic DNA

<400> SEQUENCE: 25
ggttcttgga gtagctatgg tttc 24

<210> SEQ ID NO 26
<211> LENGTH: 2699
<212> TYPE: DNA
<213> ORGANISM: Arabidopsis thaliana

<400> SEQUENCE: 26
cttatttact tttacaattg taaatagttt agagtttggc ttactgcgtc agcaaccact 60
gtaggctgct gtttaaggag catttggttt ctaagggttt catgtactgg atggaagaag 120
tcgtgcttga gagcatcctc tgcgctgatt cgtcgcctcg ggttaacggt caaacattta 180
tcaacgaggt caagaagcga tagtggaatt acgtctagaa actctctgcg ttttgtgttg 240
agttcgcacc attttctcaa ctccatcccc ttcaagtacc ttgactcgta taattcctta 300
gggaaagagg attcacggtt gtgcagcttg gctacttccc ataattcttc actgcctcgt 360
agttgtgcaa tgtcctttat gttctgttca gggtcaccag tgaaaggtgt ccttcccatt 420
atgaggtata acaaagtaac tcccgcagac cacacgtcta tcttaggtcc ttggtgcaaa 480
gatctgaagc aaacctctgg agctcggaag cctttggttc ctgagcaagg accgtctttc 540
ttctcaatta cgtcccctgc ttcaggccga ccgttagagc acagtggcat tggggtcaga 600
taaagaagtt ccttctcagc tttccctgga agagcagcta cccgttttct catagacgta 660
ggagctttgg atgatacttc atggtttgga attggaacag acattgtctc ttgcagaaaa 720

-continued tctaaaagcg cttttcttcc atgacatggc aaaggctctc ttctcttttc acctgaaggg 780
ttgttccttg tgctggtcac atctttagct gaagttaagc cagacccttc tgccccttgg 840
ctattgagtc tctcccatct ggtcatgtca ttccgagctc ttgtctttcc cgctgctttc 900
ttgatactat taggcgctaa agttttctga gaaggtttgt tggtccctcg gtttaccgca 960
tcgagtgatt taaccaatgt atgatgtttc ttgctggcgg taggaagacc tgaagctgct 1020
tttgatttat ctgctcttct gtacttctgg tgcaaatcca tggcaaggtt aaaatcaatg 1080
agatagcctt tgttggtctt cctagagaag aggaagtttc ctggcttaac atccctatga 1140
acaacaccct gcttatgcag actcgataga gctttgaaca tgcagtagcc gtaccactgc 1200
agctgataca catctatttc tctcttcaat gaatcaggtc tgtcatgttc aaggtgctca 1260
aggatgatgc aatcagaatc tccattcttg agacagcctt catgctttat tatacagttt 1320
ttccccccaa aacgctccag cattctgatt tcattattca cataatactt ctgagcgcca 1380
acatgagggc atttaattgc aaactctgtt ccatcagttt tcctcgttgc cttataaaca 1440
atcccgtagc cacctgaacc ttcttcctct acaatagtgt aagaatcaaa atctggaatt 1500
gtgttatgct ttgcctgatc cttctgatct ttaagacgaa cggtgttaaa attctgcttc 1560
ctcttctgga taactttact ttttctggtg tgttttatct caggggaaca gctgtacgtt 1620
ttgctgtttc ccggcaattt gcattgatcc agagtttttt gtaccaaaga tttatcttga 1680
ttagcttctg tagcagaagg cttcaacggc agctctctgt caggggtgct aacgatgtct 1740
acagtgtgat catctacaag tagatcttca gtgtcatcca caatctgcac tggttctaac 1800
tcattttctg ttggcatcaa tgaggcaacg ggatcggact gcacagaatc agtttgtatc 1860
tctcccttag ggaagagatc cttcttattt ttatcatcac cttcttcgat taatatttgg 1920
ttgtcagcaa tttggaaatc tccaatttca ggtcgctcgt aatatccatc ctcctgagga 1980
gatggcaaat cgttcttgct ttcctctaac cgatgtgtag gattgacatc cactgaagca 2040
ttggatgtct gcggaccagg ctgatgatct tgaacaaaag cctctattcc tcggttagat 2100
gcacttaaat tgaaaaccga agcttgggat tcaagagcta aaatagtccc aagcatagtt 2160
ccacaggcaa cagttctgat gtcgttaggt ctgctatcta ttacagagta attcacatcg 2220
tttccatcat ttcgacttct tttgggcaat ggcatgagct ctagctcctc ttgttccgca 2280
ttctctctcg aatgctttag cgtgagagat ctcggatcca taaactgttc taacacaaca 2340
ttttcctgca aatccaaact acaggcgaaa ctagccggag cggagggaga ctcaggcgag 2400
agagtcacag tgaagccatc ttcggcaagg gaaataggag aattagggat cgagcaaaga 2460
tatttgacga gattaggaga accttggaag tatgtacact ttgaagaaag atctataaca 2520
gattctggat gaccagaaga aagtaggaga cgagataact caaaagcatg cagatgatag 2580
ttaaggtcgt cgttgccgtc tgaattggtg ggactaagag gaatgagctc tcttccggct 2640
gtagaattct cgagttgacg cggttccgag ttttctgaca ttgcaaatgc tgtgaatct 2699

<210> SEQ ID NO 27
<211> LENGTH: 2512
<212> TYPE: DNA
<213> ORGANISM: Arabidopsis thaliana

<400> SEQUENCE: 27
tttttttttt tttttttttt tttttttttt tttttttttt tttttttttt tgaacaaaag 60
ttccaacttg gaaaagaaat gaaaattcaa acccaactct atacaatttt ctgtaatatt 120

-continued

```
accctctaag tttatataat cagttttgtt ttagggttag tccacaagac tgatctaaag    180
atgagaaaaa ttacagatga ctttgggtta tatgagaaac ataatctggt gtattacctg    240
cacaataaat ctacaaattt tcctccgtca ccagctcgtc tggtagtatc aacctctcca    300
tgtaagcctt tatcttgaca gcatcagatg gagaagggct taaatccaaa gcaatgccga    360
aatgtaacac ggctttgtcg tattgcttta gctgattgta tattttgcca agcgatgcat    420
ggacactgct ttcttgagga gcacattctt tgagctcttc taaaactttc tgtgctttgt    480
gataatcacc taggctggtt aatatgtgag ccttgtagta cttggggagc ggattctttg    540
catcagtgag tacagccttc tccatcatca tcaacgcctc atcgtttctc tttgactcat    600
gcaaagcaat tccatagtaa cacatgatga ctgaagatct tggatttatt tggagagcca    660
gttgaaattg atgctgcgca aactcgaatt tctcctgacg aagataggtc attccaagac    720
cgtaccatgc attatagtgt ctcgtatcta tgcccagagc cttccggtag catctctctg    780
catcctcgaa ttcttccaat gcggcaaact cgtggccaca aagggtatgt gcatatgtga    840
atctttcatt cagttggata gctctctgaa acattttgag agcagtatca tgatccttac    900
gcaaactgta acagttccca actgcacacc aggattctgg agacaggcga tcaactgaaa    960
tcagttcctg agccagatag cccaacctca tctcttcttt caggtgataa agaacagtgg   1020
agtatgtatc cattccttcc aaagcataag gatacttttg atgagcaaga gtaaaggaag   1080
agtcagcgtt gaagtagtct tgtagctcaa aatatgcttt tccaacctgc atgagaaccc   1140
agtgtgtatt gtattgtttc tgagatagct tttgatatgc caacaaagct tcctgacact   1200
tgtacatatg taaatgcctg tggccatctc caagaatttt cagaatgcct agcacttctg   1260
aaattccaga aataaggctg aaacgatccg gggaagattc actaggattt gacttttcct   1320
catcatcaac agagcttcca gtgtcactta cagactggcc tgacgtcgtt gctggatcat   1380
ttagagtaac ggtatcagga atcgcttctt tgctgctttg gattctgcat tttccaatca   1440
tcgaggaaag agaaggtgca tagtttgact cggaaggtga aagatgtaac caatgggaat   1500
cttttccaaa tgactgcgac ataggattct ttttccttgc tgctattcta gcactacggc   1560
ggcgcccaga ttcttcttga gcctctgctg acaattcttc actaaaaaag tttcttcgac   1620
gcacacgcac tccatgtaca gacatcaaag atccttccac tgctggacga cgcatattct   1680
taagaagcag aggcggtgga gcatccatta cctgtaaaag cactggagaa ggtgtgttca   1740
agtcccatcc gtttgtacta agttgcctgt cagtatttgg tggaatatct ccaggctgct   1800
gcataatttt cagatcttgt tggttctctc ctggaatgtg ttctgtttgc gataaacctg   1860
tatcttttaa ggccttatca gaatctgtaa tctggtctat ggttgctcct tctgagaagc   1920
ttattctttg ttctacacaa gttttaagac gctgggaagc aacattcccg aaaactgttg   1980
aggcttcttc agcggcacct aaactacaaa gttctccata tgcttcccaa cacaatggat   2040
caaatgacaa tgccatccta aactgttgta ttgaacagtt cttcctccca gaatatctat   2100
atataagacc aagaagataa tgcccagctg caccaccagg aacttcttca gcataatctt   2160
cacagggcaa caatgcagct tcagcctctc caagaagatc caacttaaag catgagaatg   2220
caaataaata ccgagactga ggcgtttttg aacctttaag gatataatat gcactataag   2280
cttgactgtt actcaagtaa cacctggcta acaattgcag gttcacctca gatggaaatt   2340
gggcgagaag aagttcgcaa aggaagatag cattggtgaa cataaaatgg ttaaggtttt   2400
tctggacaca attcgccagt agattctcca tcatctgatg atgatgatga ccaaattgac   2460
gagacaatcg atgttgttgt tgttcctcgg aggctgtgtg tgtaatgtcg cc           2512
```

-continued

<210> SEQ ID NO 28
<211> LENGTH: 20
<212> TYPE: DNA
<213> ORGANISM: Artificial Sequence
<220> FEATURE:
<223> OTHER INFORMATION: Synthetic DNA

<400> SEQUENCE: 28
ctctcccatc tggtcatgtc 20

<210> SEQ ID NO 29
<211> LENGTH: 20
<212> TYPE: DNA
<213> ORGANISM: Artificial Sequence
<220> FEATURE:
<223> OTHER INFORMATION: Synthetic DNA

<400> SEQUENCE: 29
gaacatgcag tagccgtacc 20

<210> SEQ ID NO 30
<211> LENGTH: 20
<212> TYPE: DNA
<213> ORGANISM: Artificial Sequence
<220> FEATURE:
<223> OTHER INFORMATION: Synthetic DNA

<400> SEQUENCE: 30
aaatggtgcg aactcaacac 20

<210> SEQ ID NO 31
<211> LENGTH: 20
<212> TYPE: DNA
<213> ORGANISM: Artificial Sequence
<220> FEATURE:
<223> OTHER INFORMATION: Synthetic DNA

<400> SEQUENCE: 31
tatgggaagt agccaagctg 20

<210> SEQ ID NO 32
<211> LENGTH: 17
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n = a, c, g, or t
<220> FEATURE:
<221> NAME/KEY: misc_feature
<222> LOCATION: (12)..(12)
<223> OTHER INFORMATION: n = a, c, g, or t

<400> SEQUENCE: 32
tgggtnttrg cnmargg 17

<210> SEQ ID NO 33
<211> LENGTH: 17
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)

-continued

```
<223> OTHER INFORMATION: n = a, c, g, or t
<220> FEATURE:
<221> NAME/KEY: misc_feature
<222> LOCATION: (15)..(15)
<223> OTHER INFORMATION: n = a, c, g, or t

<400> SEQUENCE: 33

atgganrtht wyagnac                                                 17


<210> SEQ ID NO 34
<211> LENGTH: 18
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (15)..(15)
<223> OTHER INFORMATION: n = a, c, g, or t

<400> SEQUENCE: 34

agrcaytaya aygcntgg                                                18


<210> SEQ ID NO 35
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n = a, c, g, or t

<400> SEQUENCE: 35

tadaycatnc cyaavccraa                                              20
```